United States Patent
Liu et al.

(10) Patent No.: US 11,136,596 B2
(45) Date of Patent: Oct. 5, 2021

(54) LONG-CHAIN DIBASIC ACID WITH LOW CONTENT OF HYDROXYL ACID IMPURITY AND PRODUCTION METHOD THEREOF

(71) Applicants: Cathay Biotech Inc., Shanghai (CN); CIBT America Inc., Newark, DE (US)

(72) Inventors: Wenbo Liu, Shanghai (CN); Min Xu, Shanghai (CN); Chen Yang, Shanghai (CN); Howard Chou, Shanghai (CN); Xiucai Liu, Shanghai (CN)

(73) Assignees: CIBT AMERICA INC., Newark, DE (US); CATHAY BIOTECH INC.

( * ) Notice: Subject to any disclaimer, the term of this patent is extended or adjusted under 35 U.S.C. 154(b) by 0 days.

(21) Appl. No.: 16/503,304

(22) Filed: Jul. 3, 2019

(65) Prior Publication Data

US 2020/0010855 A1    Jan. 9, 2020

(30) Foreign Application Priority Data

Jul. 6, 2018   (CN) .......................... 201810734180.4
Jul. 6, 2018   (CN) .......................... 201810734353.2
Apr. 22, 2019  (CN) .......................... 201910321631.6

(51) Int. Cl.
*C12N 1/20* (2006.01)
*C12N 15/90* (2006.01)
*C12N 9/04* (2006.01)
*C12P 7/44* (2006.01)

(52) U.S. Cl.
CPC ......... *C12N 15/905* (2013.01); *C12N 9/0006* (2013.01); *C12P 7/44* (2013.01); *C12Y 101/01001* (2013.01)

(58) Field of Classification Search
CPC ...................... C12N 7/6409; C12Y 602/01003
See application file for complete search history.

(56) References Cited

U.S. PATENT DOCUMENTS

2010/0041115 A1*  2/2010  Nicaud ................ C12N 9/0042
                                                 435/145
2020/0010855 A1*  1/2020  Liu ......................... C12N 1/16

FOREIGN PATENT DOCUMENTS

CN     107326051 A     11/2017
EP       3438271 A2      6/2019
WO    2017/015368 A1     1/2017

OTHER PUBLICATIONS

Cao et al., "High-level productivity of α,ω-dodecanedioic acid with a newly isolated *Candida viswanathii* strain", J. Ind. Microbiol Biotechnol (2017) 44:1191-1202.

Extended European Search Report for Application No. 19184878.7, dated Dec. 3, 2019, 12 pages.

Lee et al., "Biotransformation of dicarboxylic acids from vegetable oil-derived sources: current methods and suggestions for improvement", Applied Microbiology and Biotechnology (2019) 103:1545-1555.

Seo et al., "Adding value to plant oils and fatty acids: Biological transformation of fatty acids into ω-hydroxycarboxylic, α-ω-dicarboxylic, and ω-aminocarboxylic acids", Journal of Biotechnology 216 (2015) 158-166.

Werner et al., "*Candida guillietmondii* as a potential biocatalyst for the production of long-chain α-ω-dicarboxylic acids", Biotechnol Lett (2017) 39:429-438.

* cited by examiner

*Primary Examiner* — Tekchand Saidha

(74) *Attorney, Agent, or Firm* — Adsero IP

(57) ABSTRACT

The present invention relates to a long-chain dibasic acid with low content of hydroxyl acid impurity and a production method thereof, in particular to a method for producing a long-chain dibasic acid with low content of hydroxyl acid impurity by fermenting a long-chain dibasic acid producing strain prepared by homologous recombination method. The present invention relates to a recombinant long-chain dibasic acid producing microorganism, having increased alcohol dehydrogenase activity and optionally decreased acyl-CoA oxidase activity. The present invention also relates to a method of producing a long-chain dibasic acid by the recombinant long-chain dibasic acid producing microorganism and use thereof.

7 Claims, 1 Drawing Sheet

Specification includes a Sequence Listing.

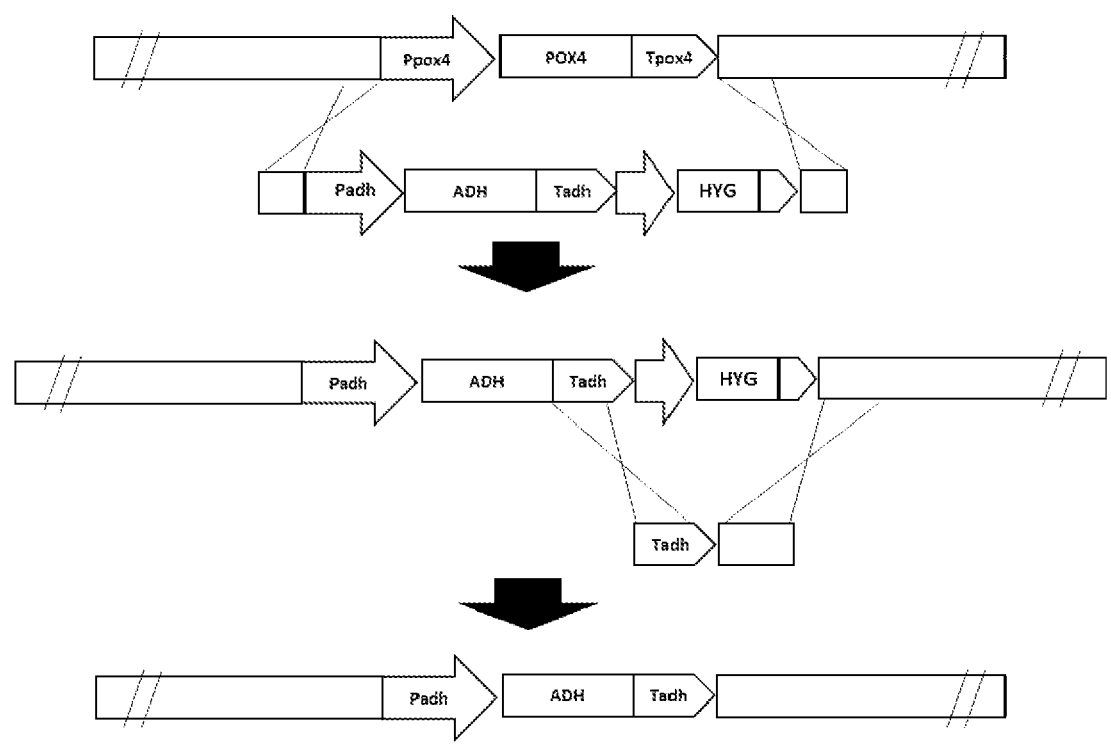

SEQUENCE LISTING

```
<160> NUMBER OF SEQ ID NOS: 31

<210> SEQ ID NO 1
<211> LENGTH: 40
<212> TYPE: DNA
<213> ORGANISM: Artificial Sequence
<220> FEATURE:
<223> OTHER INFORMATION: primer ADH-F

<400> SEQUENCE: 1
cgacggagtt agtgtccgtt gtcttggttg gtttgccagc                              40

<210> SEQ ID NO 2
<211> LENGTH: 40
<212> TYPE: DNA
<213> ORGANISM: Artificial Sequence
<220> FEATURE:
<223> OTHER INFORMATION: primer ADH-R

<400> SEQUENCE: 2
ccattttcgg gttcgcatgc aaaaacgact ggccggagat                              40

<210> SEQ ID NO 3
<211> LENGTH: 2331
<212> TYPE: DNA
<213> ORGANISM: Artificial Sequence
<220> FEATURE:
<223> OTHER INFORMATION: ADH

<400> SEQUENCE: 3
cgacggagtt agtgtccgtt gtcttggttg gtttgccagc tggtgccaag ctcgaagcac        60
ctatcttcaa tgccgttgcc aaatccatct aaatcaagga ttcttacgtg ggtaaccgaa       120
gagacactgc tgaggctgtt gatttcttcg cgaaaggttt ggtcaagtgt ccaattaagg       180
```

-continued

```
ttgttgagtt gagtgaattg ccagagattt tcaaattgtt ggaagagggt aagatcttgg      240
gtagatacgt cgttgacact gccaaataat caggcggctc cttccccaat ttacgtagat      300
gtttccgttt atagaattat attttacaca tgccccaaag caaacatttc cataattctt      360
gaacacttgt agaacacatg tgggagtcca ccccacgagc ggacatatgt gccctatttg      420
aacaataact ccggaatgtt gtgtgattac ataattacaa cccgcgcgt gggaataatt       480 taccgaggcg acacaatccc ccttttccag accaccaatg tgacatttt ggtagtattt       540 ccacaagagg aaattacaga ataatgggg ctggttggtg gtgggagtgg tacatacaac       600
attgagaacg tattcggagc caattggctg aatgagacac gataattggc cgcatgctcc      660
agggagcctg cgacacatca aatttgacag gtctgaatca atttcatcat tggttcaaat      720
aatatccgat accgtcaatc ttcttatcaa aagtggggat cttcccccaa attcagctag      780
caacgtatag cactcccccc tttccactcc ttcctagaag catatttaaa cggggatgtt      840
tctccctcga tttcttttcc aaaactgcaa aaaactttaa tcaccaaaac taactccgaa      900
acaagtatgt ccgttccaac tactcagaaa gctgttatct ttgaaaccaa tggtggcaag      960
ttagaataca aagacgtgcc ggtccctgtc cctaaaccca acgaattgct tgtcaacgtc     1020
aagtactcgg gtgtgtgtca ttctgacttg catgtctgga aaggcgactg gcccattcct     1080
gccaagttgc ccttggtggg aggtcacgaa ggtgctggtg tcgttgtcgg catgggtgac     1140
aacgtcaagg gctggaaggt gggggacttg gctggtatca agtggttgaa tggttcgtgt     1200
atgaactgtg agttttgcca acagggcgca gaacctaact gttcaagagc cgacatgtct     1260
gggtataccc acgatggaac tttccaacaa tacgccactg ctgatgctgt ccaagctgcc     1320
aagatcccag aaggcgccga catggctagt atcgccccga tcttgtgcgc tggtgtgacc     1380
gtgtacaagg ctttgaagaa cgccgacttg ttggctggcc aatgggtggc tatctctggt     1440
gctggtggtg gtttgggctc cttgggtgtg cagtacgcta aagccatggg ttacagagtg     1500
ttggctatcg acggtggtga cgagagagga gagtttgtca agtccttggg cgccgaagtg     1560
tacattgact tccttaagga acaggacatc gttagtgcta tcagaaaggc aactggtggt     1620
ggtccacacg gtgttattaa cgtgtcagtg tccgaaaagg caatcaacca gtcggtggag     1680
tacgtcagaa ctttggggaa agtggtttta gttagcttgc cggcaggtgg taaactcact     1740
gctcctcttt tcgagtctgt tgctagatca atccagatta gaactacgtg tgttggcaac     1800
agaaaggata ctactgaagc tattgatttc tttgttagag ggttgatcga ttgcccaatt     1860
aaagtcgctg gtttaagtga agtgccagag atttttgact tgatggagca gggaaagatc     1920
ttgggtagat atgtcgttga tacgtcaaag tagttatcta tattgtttcc cagaatggag     1980
atttctctaa ttgctctata ctctccgact ctatcagcac tttaccatct gtcgcatcta     2040
ggtaataaag ttcggtcaca ccaagcgatt taacgtactt ccacgtcttg tcataattca     2100
aaccaacctg ggtcaaagcg tgagcatcat ctgataaaca aaacctggcg cctccatgct     2160
ttatgattgc ctccgcaata tccctcttag gatacgacgt gtcccaccct ttccttatag     2220
ctgacgagtt caactcaaac aacccgccgt acagttttac caacttgata ttccggacaa     2280
tcaatgccca gatctccggc cagtcgtttt tgcatgcgaa cccgaaaatg g              2331
```

<210> SEQ ID NO 4
<211> LENGTH: 5873
<212> TYPE: DNA
<213> ORGANISM: Artificial Sequence
<220> FEATURE:

<223> OTHER INFORMATION: vector pCIB2

<400> SEQUENCE: 4

```
gcgcccaata cgcaaaccgc ctctcccgc gcgttggccg attcattaat gcagctggca        60
cgacaggttt cccgactgga aagcgggcag tgagcgcaac gcaattaatg tgagttagct       120
cactcattag gcaccccagg ctttacactt tatgcttccg gctcgtatgt tgtgtggaat       180
tgtgagcgga taacaatttc acacaggaaa cagctatgac catgattacg aattcggtct       240
agtatgattg tcaataatga tgggtcatcg tttcctgatt cgacgttccc tgtggtgtcg       300
ttaaatagcc tgtctgaaat ctcctccatg attgtgttgg tgtgtgttgt ttgactttcc       360
caattgctta catttttttc ttcaaggatt cgctccaaaa tagacagaaa ttatcgcgac       420
aagtcagacg aacgtcgcac gaggcgaacc aaattcttta gaagcatacg aaaactcact       480
ttatttccat tagaagtatt aaattaacaa atatataata tacaggatac aaagtaaaag       540
cacgcttaag caaccaaagc ggaagcggta gcggattcgt atttccagtt aggtggcaag       600
acagcgacgg ttctgtagta tctggccaat ctgtggattc tagattcaat caaaatcaat       660
ctgaacttgg agtccttgtc ctttctgttt cttttccaagt gctttctgac agagacagcc       720
ttcttgatca agtagtacaa gtcttctggg atttctggag ccaaaccgtt ggatttcaag       780
attctcaaga tcttgttacc agtgacaacc ttggcttggg aaacaccgtg agcatctctc       840
aagataacac caatttgaga tggagtcaaa ccctttctgg cgtacttgat gacttgttca       900
acaacttcgt cagaagacaa cttgaaccaa gatggagcgt tcttgagta tggaagagcg       960
gaggaggaaa tacctttacc ctaaaataac aagagctaat gttagtaatt tgaaaaaaaa      1020
gacgttgagc acgcacaccc catccacccc acaggtgaaa cacatcaaac gtagcaagaa      1080
caatagttgg ccctcccgtc aagggggcag gtaattgtcc aagtacttta gaaaagtatg      1140
tttttaccca taagatgaac acacacaaac cagcaaaagt atcaccttct gcttttcttg      1200
gttgaggttc aaattatgtt tggcaataat gcagcgacaa tttcaagtac ctaaagcgta      1260
tatagtaaca attctaggtc tgtatagtcg accgtaggtg aatcgtttac tttaggcaag      1320
accttgtccc tgataaagcc aggttgtact ttctattcat tgagtgtcgt ggtggtggta      1380
gtggtggttg attgggctgt tgtggtagta gtagtggttg tgatttggaa catacagatg      1440
aatgcatacg acccatgatg actgatttgt ttctttattg agttgatggt aagaaagaga      1500
agaagaggag gtaaaaaggt ggtagagtga aaaatttttt tctcttaaaa gtgagagaga      1560
gaaagagaaa aatttcactg cgaaacaaat ggttggggac acgacttttt tcaggaattt      1620
ttactcgaag cgtatatgca ggaaagttgt tgttagggaa tatggagcca caagagagct      1680
gcgaattcga gctcggtacc cggggatcct ctagagtcga cctgcaggca tgcgaacccg      1740
aaaatggagc aatcttcccc ggggcctcca ataccaact cacccgagag agagaaagag      1800
acaccaccca ccacgagacg gagtatatcc accaaggtaa gtaactcagg gttaatgata      1860
caggtgtaca cagctccttc cctagccatt gagtgggtat cacatgacac tggtaggtta      1920
caaccacgtt tagtagttat tttgtgcaat tccatgggga tcaggaagtt tggtttggtg      1980
ggtgcgtcta ctgattcccc tttgtctctg aaaatctttt ccctagtgga cactttggc       2040
tgaatgatat aaaattcacct tgattcccac cctcccttct ttctctctct ctctgttaca      2100
cccaattgaa ttttctttt tttttactt tccctcctc tttatcatca aagataagta        2160
agtttatcaa ttgcctattc agaatgaaaa agcctgaact caccgcgacg tctgtcgaga      2220
agtttctcat cgaaaagttc gacagcgtct ccgacctcat gcagctctcg gagggcgaag      2280
```

```
aatctcgtgc tttcagcttc gatgtaggag ggcgtggata tgtcctccgg gtaaatagct   2340
gcgccgatgg tttctacaaa gatcgttatg tttatcggca ctttgcatcg gccgcgctcc   2400
cgattccgga agtgcttgac attggggaat tcagcgagag cctcacctat tgcatctccc   2460
gccgtgcaca gggtgtcacg ttgcaagacc tccctgaaac cgaactcccc gctgttctcc   2520
agccggtcgc ggaggccatg gatgcgatcg ctgcggccga tcttagccag acgagcgggt   2580
tcggcccatt cggaccgcaa ggaatcggtc aatacactac atggcgtgat ttcatatgcg   2640
cgattgctga tccccatgtg tatcactggc aaactgtgat ggacgacacc gtcagtgcgt   2700
ccgtcgcgca ggctctcgat gagctcatgc tttgggccga ggactgcccc gaagtccggc   2760
acctcgtgca cgcggatttc ggctccaaca atgtcctcac ggacaatggc cgcataacag   2820
cggtcattga ctggagcgag gcgatgttcg gggattccca atacgaggtc gccaacatct   2880
tcttctggag gccgtggttg gcttgtatgg agcagcagac gcgctacttc gagcggaggc   2940
atccggagct tgcaggatcg ccgcggctcc gggcgtatat gctccgcatt ggtcttgacc   3000
aactctatca gagcttggtt gacggcaatt tcgatgatgc agcttgggcg cagggtcgat   3060
gcgacgcaat cgtccgatcc ggagccggga ctgtcgggcg tacacaaatc gcccgcagaa   3120
gcgcggccgt ctggaccgat ggctgtgtag aagtactcgc cgatagtgga aaccgacgcc   3180
ccagcactcg tccgagggca aggaatagt gtgctaccca cgcttactcc accagagcta   3240
ttaacatcag aaatatttat tctaataaat aggatgcaaa aaaaaaccc cccttaataa    3300
aaaaaaaga acgattttt tatctaatga agtctatgta tctaacaaat gtatgtatca    3360
atgtttattc cgttaaacaa aaatcagtct gtaaaaaagg ttctaaataa atattctgtc   3420
tagtgtacac attctcccaa aatagtgaaa tccagctgct agcgtgtaag cttggcactg   3480
gccgtcgttt tacaacgtcg tgactgggaa acccctggcg ttacccaact taatcgcctt   3540
gcagcacatc cccctttcgc cagctggcgt aatagcgaag aggcccgcac cgatcgccct   3600
tcccaacagt tgcgcagcct gaatggcgaa tggcgcctga tgcggtattt tctccttacg   3660
catctgtgcg gtatttcaca ccgcatatgg tgcactctca gtacaatctg ctctgatgcc   3720
gcatagttaa gccagccccg acacccgcca acacccgctg acgcgccctg acgggcttgt   3780
ctgctcccgg catccgctta cagacaagct gtgaccgtct ccgggagctg catgtgtcag   3840
aggttttcac cgtcatcacc gaaacgcgcg agacgaaagg gcctcgtgat acgcctattt   3900
ttataggtta atgtcatgat aataatggtt tcttagacgt caggtggcac ttttcgggga   3960
aatgtgcgcg gaacccctat ttgtttattt ttctaaatac attcaaatat gtatccgctc   4020
atgagacaat aaccctgata aatgcttcaa taatattgaa aaaggaagag tatgagtatt   4080
caacatttcc gtgtcgccct tattcccttt tttgcggcat tttgccttcc tgttttgct    4140
cacccagaaa cgctggtgaa agtaaaagat gctgaagatc agttgggtgc acgagtgggt   4200
tacatcgaac tggatctcaa cagcggtaag atccttgaga gttttcgccc cgaagaacgt   4260
tttccaatga tgagcacttt taaagttctg ctatgtggcg cggtattatc ccgtattgac   4320
gccgggcaag agcaactcgg tcgccgcata cactattctc agaatgactt ggttgagtac   4380
tcaccagtca cagaaaagca tcttacggat ggcatgacag taagagaatt atgcagtgct   4440
gccataacca tgagtgataa cactgcggcc aacttacttc tgacaacgat cggaggaccg   4500
aaggagctaa ccgcttttt gcacaacatg ggggatcatg taactcgcct tgatcgttgg   4560
gaaccggagc tgaatgaagc cataccaaac gacgagcgtg acaccacgat gcctgtagca   4620
```

```
atggcaacaa cgttgcgcaa actattaact ggcgaactac ttactctagc ttcccggcaa      4680
caattaatag actggatgga ggcggataaa gttgcaggac cacttctgcg ctcggccctt      4740
ccggctggct ggtttattgc tgataaatct ggagccggtg agcgtgggtc tcgcggtatc      4800
attgcagcac tggggccaga tggtaagccc tcccgtatcg tagttatcta cacgacgggg      4860
agtcaggcaa ctatggatga acgaaataga cagatcgctg agataggtgc ctcactgatt      4920
aagcattggt aactgtcaga ccaagtttac tcatatatac tttagattga tttaaaactt      4980
catttttaat ttaaaaggat ctaggtgaag atccttttg ataatctcat gaccaaaatc       5040
ccttaacgtg agttttcgtt ccactgagcg tcagacccccg tagaaaagat caaaggatct     5100
tcttgagatc cttttttttct gcgcgtaatc tgctgcttgc aaacaaaaaa accaccgcta     5160
ccagcggtgg tttgtttgcc ggatcaagag ctaccaactc tttttccgaa ggtaactggc      5220
ttcagcagag cgcagatacc aaatactgtc cttctagtgt agccgtagtt aggccaccac      5280
ttcaagaact ctgtagcacc gcctacatac ctcgctctgc taatcctgtt accagtggct      5340
gctgccagtg gcgataagtc gtgtcttacc gggttggact caagacgata gttaccggat      5400
aaggcgcagc ggtcgggctg aacgggggt tcgtgcacac agcccagctt ggagcgaacg       5460
acctacaccg aactgagata cctacagcgt gagctatgag aaagcgccac gcttcccgaa      5520
gggagaaagg cggacaggta tccggtaagc ggcagggtcg gaacaggaga gcgcacgagg      5580
gagcttccag ggggaaacgc ctggtatctt tatagtcctg tcgggtttcg ccacctctga      5640
cttgagcgtc gatttttgtg atgctcgtca ggggggcgga gcctatggaa aaacgccagc      5700
aacgcggcct ttttacggtt cctggccttt tgctggcctt ttgctcacat gttctttcct      5760
gcgttatccc ctgattctgt ggataaccgt attaccgcct ttgagtgagc tgataccgct      5820
cgccgcagcc gaacgaccga gcgcagcgag tcagtgagcg aggaagcgga aga             5873
```

```
<210> SEQ ID NO 5
<211> LENGTH: 40
<212> TYPE: DNA
<213> ORGANISM: Artificial Sequence
<220> FEATURE:
<223> OTHER INFORMATION: primer Tadh_HYG-F

<400> SEQUENCE: 5
atctccggcc agtcgttttt gcatgcgaac ccgaaaatgg                             40

<210> SEQ ID NO 6
<211> LENGTH: 40
<212> TYPE: DNA
<213> ORGANISM: Artificial Sequence
<220> FEATURE:
<223> OTHER INFORMATION: primer POX4_HYG-R

<400> SEQUENCE: 6
ctaagggttt ttccggggct gctagcagct ggatttcact                             40

<210> SEQ ID NO 7
<211> LENGTH: 1776
<212> TYPE: DNA
<213> ORGANISM: Artificial Sequence
<220> FEATURE:
<223> OTHER INFORMATION: HYG

<400> SEQUENCE: 7
atctccggcc agtcgttttt gcatgcgaac ccgaaaatgg agcaatcttc cccggggcct      60
ccaaatacca actcacccga gagagataaa gagacaccac ccaccacgag acggagtata     120
```

```
tccaccaagg taagtaactc agagttaatg atacaggtgt acacagctcc ttccctagcc      180
attgagtggg tatcacatga cactggtagg ttacaaccac gtttagtagt tattttgtgc      240
aattccatgg ggatcaggaa gtttggtttg gtgggtgcgt ctactgattc ccctttgtct      300
ctgaaaatct tttccctagt ggaacacttt ggctgaatga tataaattca ccttgattcc      360
caccctccct tctttctctc tctctctgtt acacccaatt gaattttctt ttttttttta      420 cttccctcc ttctttatca tcaaagataa gtaagtttat caattgccta ttcagaatga      480
aaaagcctga actcaccgcg acgtctgtcg agaagtttct catcgaaaag ttcgacagcg      540
tctccgacct catgcagctc tcggagggcg aagaatctcg tgctttcagc ttcgatgtag      600
gagggcgtgg atatgtcctc cgggtaaata gctgcgccga tggtttctac aaagatcgtt      660
atgtttatcg gcactttgca tcggccgcgc tcccgattcc ggaagtgctt gacattgggg      720
aattcagcga gagcctcacc tattgcatct cccgccgtgc acagggtgtc acgttgcaag      780
acctccctga aaccgaactc cccgctgttc tccagccggt cgcggaggcc atggatgcga      840
tcgctgcggc cgatcttagc cagacgagcg ggttcggccc attcggaccg caaggaatcg      900
gtcaatacac tacatggcgt gatttcatat gcgcgattgc tgatccccat gtgtatcact      960
ggcaaactgt gatggacgac accgtcagtg cgtccgtcgc gcaggctctc gatgagctca     1020
tgctttgggc cgaggactgc cccgaagtcc ggcacctcgt gcacgcggat ttcggctcca     1080
acaatgtcct cacggacaat ggccgcataa cagcggtcat tgactggagc gaggcgatgt     1140
tcggggattc ccaatacgag gtcgccaaca tcttcttctg gaggccgtgg ttggcttgta     1200
tggagcagca gacgcgctac ttcgagcgga ggcatccgga gcttgcagga tcgccgcggc     1260
tccgggcgta tatgctccgc attggtcttg accaactcta tcagagcttg gttgacggca     1320
atttcgatga tgcagcttgg gcgcagggtc gatgcgacgc aatcgtccga tccggagccg     1380
ggactgtcgg gcgtacacaa atcgcccgca gaagcgcggc cgtctggacc gatggctgtg     1440
tagaagtact cgccgatagt ggaaaccgac gccccagcac tcgtccgagg gcaaaggaat     1500
agtgtgctac ccacgcttac tccaccagag ctattaacat cagaaatatt tattctaata     1560
aataggatgc aaaaaaaaaa ccccccttaa taaaaaaaaa agaaacgatt ttttatctaa     1620
tgaagtctat gtatctaaca aatgtatgta tcaatgttta ttccgttaaa caaaaatcag     1680
tctgtaaaaa aggttctaaa taatatattct gtcagtgta cacattctcc caaaatagtg     1740
aaatccagct gctagcagcc ccggaaaaac ccttag                                1776
```

<210> SEQ ID NO 8
<211> LENGTH: 20
<212> TYPE: DNA
<213> ORGANISM: Artificial Sequence
<220> FEATURE:
<223> OTHER INFORMATION: primer POX4_Up-F

<400> SEQUENCE: 8

```
cccccacctt ttgtctctgg                                                    20
```

<210> SEQ ID NO 9
<211> LENGTH: 20
<212> TYPE: DNA
<213> ORGANISM: Artificial Sequence
<220> FEATURE:
<223> OTHER INFORMATION: primer POX4_Up-R

<400> SEQUENCE: 9

```
aacggacact aactccgtcg                                                     20

<210> SEQ ID NO 10
<211> LENGTH: 20
<212> TYPE: DNA
<213> ORGANISM: Artificial Sequence
<220> FEATURE:
<223> OTHER INFORMATION: primer POX4_Down-F

<400> SEQUENCE: 10
agccccggaa aaacccttag                                                     20

<210> SEQ ID NO 11
<211> LENGTH: 20
<212> TYPE: DNA
<213> ORGANISM: Artificial Sequence
<220> FEATURE:
<223> OTHER INFORMATION: primer POX4_Down-R

<400> SEQUENCE: 11
gagacgtggg ggtaaggttg                                                     20

<210> SEQ ID NO 12
<211> LENGTH: 72
<212> TYPE: DNA
<213> ORGANISM: Artificial Sequence
<220> FEATURE:
<223> OTHER INFORMATION: POX4_Up

<400> SEQUENCE: 12
cccccacctt tgtctctgg tggtggtaag ccgacagaaa ggaaaaataa ggcgacggag           60
ttagtgtccg tt                                                             72

<210> SEQ ID NO 13
<211> LENGTH: 77
<212> TYPE: DNA
<213> ORGANISM: Artificial Sequence
<220> FEATURE:
<223> OTHER INFORMATION: POX4_Down

<400> SEQUENCE: 13
agccccggaa aaacccttag ttgatagttg cgaatttagg tcgacctctc atgatttcaa         60
ccttaccccc acgtctc                                                        77

<210> SEQ ID NO 14
<211> LENGTH: 4176
<212> TYPE: DNA
<213> ORGANISM: Artificial Sequence
<220> FEATURE:
<223> OTHER INFORMATION: complete recombination template

<400> SEQUENCE: 14
cccccacctt tgtctctgg tggtggtaag ccgacagaaa ggaaaaataa ggcgacggag           60
ttagtgtccg ttgtcttggt tggtttgcca gctggtgcca agctcgaagc acctatcttc        120
aatgccgttg ccaaatccat ctaaatcaag gattcttacg tgggtaaccg aagagacact        180
gctgaggctg ttgatttctt cgcgaaaggt ttggtcaagt gtccaattaa ggttgttgag        240
ttgagtgaat tgccagagat tttcaaattg ttggaagagg gtaagatctt gggtagatac        300
gtcgttgaca ctgccaaata atcaggcggc tccttcccca atttacgtag atgtttccgt        360
ttatagaatt atattttaca catgccccaa agcaaacatt tccataattc ttgaacactt        420
gtagaacaca tgtgggagtc caccccacga gcggacatat gtgccctatt tgaacaataa        480
```

```
ctccggaatg ttgtgtgatt acataattac aaccccgcgc gtgggaataa tttaccgagg    540
cgacacaatc cccctttcc agaccaccaa tggtgacatt ttggtagtat ttccacaaga     600
ggaaattaca gaataatgg ggctggttgg tggtgggagt ggtacataca acattgagaa     660
cgtattcgga gccaattggc tgaatgagac acgataattg gccgcatgct ccagggagcc    720
tgcgacacat caaatttgac aggtctgaat caatttcatc attggttcaa ataatatccg    780
ataccgtcaa tcttcttatc aaaagtgggg atctttcccc aaattcagct agcaacgtat    840
agcactcccc cctttccact ccttcctaga agcatattta aacggggatg tttctccctc    900
gatttctttt ccaaaactgc aaaaaactttt aatcaccaaa actaactccg aaacaagtat   960
gtccgttcca actactcaga aagctgttat ctttgaaacc aatggtggca agttagaata   1020
caaagacgtg ccggtccctg tccctaaacc caacgaattg cttgtcaacg tcaagtactc   1080
gggtgtgtgt cattctgact tgcatgtctg gaaaggcgac tggcccattc ctgccaagtt   1140
gcccttggtg ggaggtcacg aaggtgctgg tgtcgttgtc ggcatgggtg acaacgtcaa   1200
gggctggaag gtgggggact tggctggtat caagtggttg aatggttcgt gtatgaactg   1260
tgagttttgc caacagggcg cagaacctaa ctgttcaaga gccgacatgt ctgggtatac   1320
ccacgatgga actttccaac aatacgccac tgctgatgct gtccaagctg ccaagatccc   1380
agaaggcgcc gacatggcta gtatcgcccc gatcttgtgc gctggtgtga ccgtgtacaa   1440
ggctttgaag aacgccgact tgttggctgg ccaatgggtg gctatctctg tgctggtgg    1500 tggtttgggc tccttgggtg tgcagtacgc taaagccatg ggttacagag tgttggctat   1560
cgacggtggt gacgagagag gagagtttgt caagtccttg ggcgccgaag tgtacattga   1620
cttccttaag gaacaggaca tcgttagtgc tatcagaaag gcaactggtg gtggtccaca   1680
cggtgttatt aacgtgtcag tgtccgaaaa ggcaatcaac cagtcggtgg agtacgtcag   1740
aactttgggg aaagtggttt tagttagctt gccggcaggt ggtaaactca ctgctcctct   1800
tttcgagtct gttgctagat caatccagat tagaactacg tgtgttggca acagaaagga   1860
tactactgaa gctattgatt tctttgttag agggttgatc gattgcccaa ttaaagtcgc   1920
tggtttaagt gaagtgccag agattttga cttgatggag cagggaaaga tcttgggtag   1980
atatgtcgtt gatacgtcaa agtagttatc tatattgttt cccagaatgg agatttctct   2040
aattgctcta tactctccga ctctatcagc actttaccat ctgtcgcatc taggtaataa   2100
agttcggtca caccaagcga tttaacgtac ttccacgtct tgtcataatt caaaccaacc   2160
tgggtcaaag cgtgagcatc atctgataaa caaaacctgg cgcctccatg ctttatgatt   2220
gcctccgcaa tatccctctt aggatacgac gtgtcccacc ctttccttat agctgacgag   2280
ttcaactcaa acaacccgcc gtacagtttt accaacttga tattccggac aatcaatgcc   2340
cagatctccg gccagtcgtt tttgcatgcg aacccgaaaa tggagcaatc ttccccgggg   2400
cctccaaata ccaactcacc cgagagagat aaagagacac cacccaccac gagacggagt   2460
atatccacca aggtaagtaa ctcagagtta atgatacagg tgtacacagc tccttcccta   2520
gccattgagt gggtatcaca tgacactggt aggttacaac cacgtttagt agttattttg   2580
tgcaattcca tggggatcag gaagtttggt ttggtgggtg cgtctactga ttccccttg    2640 tctctgaaaa tcttttccct agtggaacac tttggctgaa tgatataaat tcaccttgat   2700
tcccaccctc ccttctttct ctctctctct gttacaccca attgaatttt cttttttttt   2760
ttactttccc tccttcttta tcatcaaaga taagtaagtt tatcaattgc ctattcagaa   2820
```

```
tgaaaaagcc tgaactcacc gcgacgtctg tcgagaagtt tctcatcgaa aagttcgaca    2880
gcgtctccga cctcatgcag ctctcggagg gcgaagaatc tcgtgctttc agcttcgatg    2940
taggagggcg tggatatgtc ctccgggtaa atagctgcgc cgatggtttc tacaaagatc    3000
gttatgttta tcggcacttt gcatcggccg cgctcccgat tccggaagtg cttgacattg    3060
gggaattcag cgagagcctc acctattgca tctcccgccg tgcacagggt gtcacgttgc    3120
aagacctccc tgaaaccgaa ctccccgctg ttctccagcc ggtcgcggag gccatggatg    3180
cgatcgctgc ggccgatctt agccagacga gcgggttcgg cccattcgga ccgcaaggaa    3240
tcggtcaata cactacatgg cgtgatttca tatgcgcgat tgctgatccc catgtgtatc    3300
actggcaaac tgtgatggac gacaccgtca gtgcgtccgt cgcgcaggct ctcgatgagc    3360
tcatgctttg ggccgaggac tgccccgaag tccggcacct cgtgcacgcg gatttcggct    3420
ccaacaatgt cctcacggac aatggccgca taacagcggt cattgactgg agcgaggcga    3480
tgttcgggga ttcccaatac gaggtcgcca acatcttctt ctggaggccg tggttggctt    3540
gtatggagca gcagacgcgc tacttcgagc ggaggcatcc ggagcttgca ggatcgccgc    3600
ggctccgggc gtatatgctc cgcattggtc ttgaccaact ctatcagagc ttggttgacg    3660
gcaatttcga tgatgcagct tgggcgcagg tcgatgcga cgcaatcgtc cgatccggag    3720
ccgggactgt cgggcgtaca caaatcgccc gcagaagcgc ggccgtctgg accgatggct    3780
gtgtagaagt actcgccgat agtggaaacc gacgcccag cactcgtccg agggcaaagg    3840
aatagtgtgc tacccacgct tactccacca gagctattaa catcagaaat atttattcta    3900
ataaatagga tgcaaaaaaa aaccccccct taataaaaaa aaagaaacg attttttatc    3960 taatgaagtc tatgtatcta acaaatgtat gtatcaatgt ttattccgtt aaacaaaaat    4020
cagtctgtaa aaaaggttct aaataaatat tctgtctagt gtacacattc tcccaaaata    4080
gtgaaatcca gctgctagca gccccggaaa aacccttagt tgatagttgc gaatttaggt    4140
cgacctctca tgatttcaac cttacccca cgtctc                              4176
```

<210> SEQ ID NO 15
<211> LENGTH: 20
<212> TYPE: DNA
<213> ORGANISM: Artificial Sequence
<220> FEATURE:
<223> OTHER INFORMATION: primer Pox4_Up-F

<400> SEQUENCE: 15
gtggtggtaa gccgacagaa                                                20

<210> SEQ ID NO 16
<211> LENGTH: 20
<212> TYPE: DNA
<213> ORGANISM: Artificial Sequence
<220> FEATURE:
<223> OTHER INFORMATION: primer ADH-2R

<400> SEQUENCE: 16
aacagcctca gcagtgtctc                                                20

<210> SEQ ID NO 17
<211> LENGTH: 20
<212> TYPE: DNA
<213> ORGANISM: Artificial Sequence
<220> FEATURE:
<223> OTHER INFORMATION: primer Tadh-F

<400> SEQUENCE: 17
gagggttgat cgattgccca                                            20

<210> SEQ ID NO 18
<211> LENGTH: 18
<212> TYPE: DNA
<213> ORGANISM: Artificial Sequence
<220> FEATURE:
<223> OTHER INFORMATION: primer Tadh-R

<400> SEQUENCE: 18
aaaaacgact ggccggag                                              18

<210> SEQ ID NO 19
<211> LENGTH: 474
<212> TYPE: DNA
<213> ORGANISM: Artificial Sequence
<220> FEATURE:
<223> OTHER INFORMATION: DNA fragment for removing resistance marker

<400> SEQUENCE: 19
gagggttgat cgattgccca attaaagtcg ctggtttaag tgaagtgcca gagattttg    60 acttgatgga gcagggaaag atcttgggta gatatgtcgt tgatacgtca aagtagttat  120
ctatattgtt tcccagaatg gagatttctc taattgctct atactctccg actctatcag  180
cactttacca tctgtcgcat ctaggtaata aagttcggtc acaccaagcg atttaacgta  240
cttccacgtc ttgtcataat tcaaaccaac ctgggtcaaa gcgtgagcat catctgataa  300
acaaaacctg gcgcctccat gctttatgat tgcctccgca atatccctct taggatacga  360
cgtgtcccac cctttcctta tagctgacga gttcaactca acaacccgc cgtacagttt   420 taccaacttg atattccgga caatcaatgc ccagatctcc ggccagtcgt tttt         474

<210> SEQ ID NO 20
<211> LENGTH: 551
<212> TYPE: DNA
<213> ORGANISM: Artificial Sequence
<220> FEATURE:
<223> OTHER INFORMATION: homologous recombination template with
      resistance marker removed

<400> SEQUENCE: 20
gagggttgat cgattgccca attaaagtcg ctggtttaag tgaagtgcca gagattttg    60 acttgatgga gcagggaaag atcttgggta gatatgtcgt tgatacgtca aagtagttat  120
ctatattgtt tcccagaatg gagatttctc taattgctct atactctccg actctatcag  180
cactttacca tctgtcgcat ctaggtaata aagttcggtc acaccaagcg atttaacgta  240
cttccacgtc ttgtcataat tcaaaccaac ctgggtcaaa gcgtgagcat catctgataa  300
acaaaacctg gcgcctccat gctttatgat tgcctccgca atatccctct taggatacga  360
cgtgtcccac cctttcctta tagctgacga gttcaactca acaacccgc cgtacagttt   420 taccaacttg atattccgga caatcaatgc ccagatctcc ggccagtcgt ttttagcccc  480
ggaaaaaccc ttagttgata gttgcgaatt taggtcgacc tctcatgatt tcaaccttac  540
ccccacgtct c                                                      551

<210> SEQ ID NO 21
<211> LENGTH: 20
<212> TYPE: DNA
<213> ORGANISM: Artificial Sequence
<220> FEATURE:
<223> OTHER INFORMATION: primer HYG-F

```
<400> SEQUENCE: 21
ctcggagggc gaagaatctc                                              20

<210> SEQ ID NO 22
<211> LENGTH: 20
<212> TYPE: DNA
<213> ORGANISM: Artificial Sequence
<220> FEATURE:
<223> OTHER INFORMATION: primer HYG-R

<400> SEQUENCE: 22
caatgaccgc tgttatgcgg                                              20

<210> SEQ ID NO 23
<211> LENGTH: 20
<212> TYPE: DNA
<213> ORGANISM: Artificial Sequence
<220> FEATURE:
<223> OTHER INFORMATION: primer Up-F

<400> SEQUENCE: 23
ttagaccgcc agagaaggga                                              20

<210> SEQ ID NO 24
<211> LENGTH: 20
<212> TYPE: DNA
<213> ORGANISM: Artificial Sequence
<220> FEATURE:
<223> OTHER INFORMATION: primer Up-R

<400> SEQUENCE: 24
tgtcattgcg taacgtggga                                              20

<210> SEQ ID NO 25
<211> LENGTH: 20
<212> TYPE: DNA
<213> ORGANISM: Artificial Sequence
<220> FEATURE:
<223> OTHER INFORMATION: primer Down-F

<400> SEQUENCE: 25
gtggtgggtt cccagcttat                                              20

<210> SEQ ID NO 26
<211> LENGTH: 20
<212> TYPE: DNA
<213> ORGANISM: Artificial Sequence
<220> FEATURE:
<223> OTHER INFORMATION: primer Down-R

<400> SEQUENCE: 26
ggaggtacca acaatccccg                                              20

<210> SEQ ID NO 27
<211> LENGTH: 40
<212> TYPE: DNA
<213> ORGANISM: Artificial Sequence
<220> FEATURE:
<223> OTHER INFORMATION: primer ADH-2F

<400> SEQUENCE: 27
tcccacgtta cgcaatgaca gtcttggttg gtttgccagc                        40

<210> SEQ ID NO 28
```

```
<211> LENGTH: 40
<212> TYPE: DNA
<213> ORGANISM: Artificial Sequence
<220> FEATURE:
<223> OTHER INFORMATION: primer HYG-2R

<400> SEQUENCE: 28
ataagctggg aacccaccac gctagcagct ggatttcact                          40

<210> SEQ ID NO 29
<211> LENGTH: 6099
<212> TYPE: DNA
<213> ORGANISM: Artificial Sequence
<220> FEATURE:
<223> OTHER INFORMATION: PCR product

<400> SEQUENCE: 29
ttagaccgcc agagaaggga gtgggaaggc agaaaaatag tccggtattt tatgtatggc     60 ataaggagt gtgtatagag acagaagaat aaaaatttca ggtttggttt atgtgtcgtt    120
tcggttgtag actaatggac gttgatgatc tctcatcatg atagccatcg ccacctcaa    180 atgatcgtga gacgcaaagg ctgaaatagg gttgagggtt gcttgattag acgagcattc    240
tgagctgttg tattctgtcg ttgatccctg gggctatctc tgctgatcgt caaacaagac    300
agccaaaaaa aacatccacc cactggtcag tggggctgta tgcaggcgta cgggtaaata    360
atttgtacgt tttaggaaac cattgtgcac aaaaagctaa agaaatctta acgagtggtt    420
aacctgtgta acagaggagg gagggaaaaa atttggccac aaacacacag acagaattat    480
tttacaagct agacaaccaa gtcaacccta gcccaactta atttcataga aaaatcaacc    540
aatcctattg tttgccaaaa taatttatag cccatgtaat agaatctctt gtctgtccaa    600
tttaaatact ttttgtactt atctcaaagt taacatcacc tgcttagcca taatccaggg    660
ttaacattct catccccacc accaccctca taactgtggg tcgcctgaga ttttcacat    720 aaatttttca cagatttccc ttgaaccaat ttttttttt cctttgatt ttctggattt    780 ttttttttta caaccactgc tttagacgat ctctagctgg ttttctttct atttcattgc    840
ctgggtagtc gccgtaacca tttcccacct tcccattcta acagtcaca gggtcctcct    900 caaacaacag cggtatgact tggattagaa cagaattctt gatcaaaggg aagatcatca    960 aaccctttt gcccaacgat aagcatccca cgttacgcaa tgacagtctt ggttggtttg   1020
ccagctggtg ccaagctcga agcacctatc ttcaatgccg ttgccaaatc catctaaatc   1080
aaggattctt acgtgggtaa ccgaagagac actgctgagg ctgttgattt cttcgcgaaa   1140
ggtttggtca agtgtccaat taaggttgtt gagttgagtg aattgccaga gatttcaaa   1200 ttgttggaag agggtaagat cttgggtaga tacgtcgttg acactgccaa ataatcaggc   1260
ggctccttcc ccaatttacg tagatgtttc cgtttataga attatatttt acacatgccc   1320
caaagcaaac atttccataa ttcttgaaca cttgtagaac acatgtggga gtccacccca   1380
cgagcggaca tatgtgccct atttgaacaa taactccgga atgttgtgtg attacataat   1440
tacaaccccg cgcgtgggaa taatttaccg aggcgacaca atccccccttt tccagaccac   1500 caatggtgac atttttggtag tatttccaca agaggaaatt acagaaataa tggggctggt   1560
tggtggtggg agtggtacat acaacattga gaacgtattc ggagccaatt ggctgaatga   1620
gacacgataa ttggccgcat gctccaggga gcctgcgaca catcaaattt gacaggtctg   1680
aatcaatttc atcattggtt caataatat ccgataccgt caatcttctt atcaaaagtg   1740
gggatctttc cccaaattca gctagcaacg tatagcactc cccccttttcc actccttcct   1800
```

```
agaagcatat ttaaacgggg atgtttctcc ctcgatttct tttccaaaac tgcaaaaaac   1860
tttaatcacc aaaactaact ccgaaacaag tatgtccgtt ccaactactc agaaagctgt   1920
tatctttgaa accatggtg gcaagttaga atacaaagac gtgccggtcc ctgtccctaa    1980
acccaacgaa ttgcttgtca acgtcaagta ctcgggtgtg tgtcattctg acttgcatgt   2040
ctggaaaggc gactggccca ttcctgccaa gttgcccttg gtgggaggtc acgaaggtgc   2100
tggtgtcgtt gtcggcatgg gtgacaacgt caagggctgg aaggtggggg acttggctgg   2160
tatcaagtgg ttgaatggtt cgtgtatgaa ctgtgagttt tgccaacagg gcgcagaacc   2220
taactgttca agagccgaca tgtctgggta tacccacgat ggaactttcc aacaatacgc   2280
cactgctgat gctgtccaag ctgccaagat cccagaaggc gccgacatgg ctagtatcgc   2340
cccgatcttg tgcgctggtg tgaccgtgta caaggctttg aagaacgccg acttgttggc   2400
tggccaatgg gtggctatct ctggtgctgg tggtggtttg ggctccttgg gtgtgcagta   2460
cgctaaagcc atgggttaca gagtgttggc tatcgacggt ggtgacgaga gaggagagtt   2520
tgtcaagtcc ttgggcgccg aagtgtacat tgacttcctt aaggaacagg acatcgttag   2580
tgctatcaga aaggcaactg gtggtggtcc acacggtgtt attaacgtgt cagtgtccga   2640
aaaggcaatc aaccagtcgg tggagtacgt cagaactttg gggaaagtgg ttttagttag   2700
cttgccggca ggtggtaaac tcactgctcc tcttttcgag tctgttgcta gatcaatcca   2760
gattagaact acgtgtgttg gcaacagaaa ggatactact gaagctattg atttctttgt   2820
tagagggttg atcgattgcc caattaaagt cgctggttta agtgaagtgc cagagatttt   2880
tgacttgatg gagcagggaa agatcttggg tagatatgtc gttgatacgt caaagtagtt   2940
atctatattg tttcccagaa tggagatttc tctaattgct ctatactctc cgactctatc   3000
agcactttac catctgtcgc atctaggtaa taaagttcgg tcacaccaag cgatttaacg   3060
tacttccacg tcttgtcata attcaaacca acctgggtca aagcgtgagc atcatctgat   3120
aaacaaaacc tggcgcctcc atgctttatg attgcctccg caatatccct cttaggatac   3180
gacgtgtccc accctttcct tatagctgac gagttcaact caaacaaccc gccgtacagt   3240
tttaccaact tgatattccg gacaatcaat gcccagatct ccggccagtc gttttttgcat  3300
gcgaacccga aaatggagca atcttccccg gggcctccaa ataccaactc acccgagaga   3360
gataaagaga caccacccac cacgagacgg agtatatcca ccaaggtaag taactcagag   3420
ttaatgatac aggtgtacac agctccttcc ctagccattg agtgggtatc acatgacact   3480
ggtaggttac aaccacgttt agtagttatt ttgtgcaatt ccatggggat caggaagttt   3540
ggtttggtgg gtgcgtctac tgattcccct ttgtctctga aaatcttttc cctagtggaa   3600
cactttggct gaatgatata aattcacctt gattcccacc ctcccttctt tctctctctc   3660
tctgttacac ccaattgaat tttcttttt ttttactttt ccctccttct ttatcatcaa    3720
agataagtaa gttatcaat tgcctattca gaatgaaaaa gcctgaactc accgcgacgt     3780
ctgtcgagaa gtttctcatc gaaaagttcg acagcgtctc cgacctcatg cagctctcgg   3840
agggcgaaga atctcgtgct ttcagcttcg atgtaggagg cgtggatat gtcctccggg    3900
taaatagctg cgccgatggt ttctacaaag atcgttatgt ttatcggcac tttgcatcgg   3960
ccgcgctccc gattccggaa gtgcttgaca ttggggaatt cagcgagagc ctcacctatt   4020
gcatctcccg ccgtgcacag ggtgtcacgt tgcaagacct ccctgaaacc gaactccccg   4080
ctgttctcca gccggtcgcg gaggccatgg atgcgatcgc tgcggccgat cttagccaga   4140
```

|  |  |  |  |  |
|---|---|---|---|---|
| cgagcgggtt | cggcccattc | ggaccgcaag | gaatcggtca | atacactaca tggcgtgatt | 4200 |
| tcatatgcgc | gattgctgat | ccccatgtgt | atcactggca | aactgtgatg gacgacaccg | 4260 |
| tcagtgcgtc | cgtcgcgcag | gctctcgatg | agctcatgct | ttgggccgag gactgccccg | 4320 |
| aagtccggca | cctcgtgcac | gcggatttcg | gctccaacaa | tgtcctcacg gacaatggcc | 4380 |
| gcataacagc | ggtcattgac | tggagcgagg | cgatgttcgg | ggattcccaa tacgaggtcg | 4440 |
| ccaacatctt | cttctggagg | ccgtggttgg | cttgtatgga | gcagcagacg cgctacttcg | 4500 |
| agcggaggca | tccggagctt | gcaggatcgc | cgcggctccg | ggcgtatatg ctccgcattg | 4560 |
| gtcttgacca | actctatcag | agcttggttg | acggcaattt | cgatgatgca gcttgggcgc | 4620 |
| agggtcgatg | cgacgcaatc | gtccgatccg | gagccgggac | tgtcgggcgt acacaaatcg | 4680 |
| cccgcagaag | cgcggccgtc | tggaccgatg | gctgtgtaga | agtactcgcc gatagtggaa | 4740 |
| accgacgccc | cagcactcgt | ccgagggcaa | aggaatagtg | tgctacccac gcttactcca | 4800 |
| ccagagctat | taacatcaga | aatatttatt | ctaataaata | ggatgcaaaa aaaaaacccc | 4860 |
| ccttaataaa | aaaaaagaa | acgattttt | atctaatgaa | gtctatgtat ctaacaaatg | 4920 |
| tatgtatcaa | tgtttattcc | gttaaacaaa | aatcagtctg | taaaaaaggt tctaaataaa | 4980 |
| tattctgtct | agtgtacaca | ttctcccaaa | atagtgaaat | ccagctgcta gcgtggtggg | 5040 |
| ttcccagctt | atttgaccaa | catcagtcaa | atctttgaag | gtcaggcatt cgaacacttg | 5100 |
| acgtcgttcc | atcagagaat | cttgaaaata | tacccaggtg | ctaaaatcat cactgatgac | 5160 |
| gacgaagcta | agcaattgag | tgaaagcaga | acgaatggta | gattcttgca catcaagact | 5220 |
| gttgaaccag | tgtatgaatt | ctccgacaaa | ttgctttaca | cttctgttgg tgtcagaaag | 5280 |
| tatgctagag | acaaggatct | tcgttcgttt | gtgtccacca | aagtcattcc tggatcaact | 5340 |
| tctgttttgg | atatgtggac | tcagcaaact | acgtaccatt | cttggttgtc attcccaaca | 5400 |
| cttatgaaca | gatcattcat | taaggaagtc | aagtctgtca | agttgtctcc gttggagaat | 5460 |
| ggtatcagaa | tcattgccga | caagaacaat | gctttgattg | agttggaagc tgctgtcgtc | 5520 |
| aaaaagtcta | ctgaaaagag | tgactacact | gagcagttga | atgacttgtc aaggcagttg | 5580 |
| gctggaactg | tcgattcccc | tgtcaatggt | ggcgttggtc | agtaccgtgc attcttacg | 5640 |
| gatgccaagt | acggaatcaa | ggaagaagac | atcaagaagg | ttgctttatt gcgcgatgcc | 5700 |
| ttcaacgacc | ttgccatgat | tttgtaccgt | tgtttgaatt | tgcatggaag attcattggt | 5760 |
| ccaactatga | aggtgtcgca | caatgcattg | gttgaattgt | tcaacaagaa ctttaaggag | 5820 |
| gaaattgttg | ccttgagatt | gggcgaagaa | gctcctaaac | ctgtgccatc gagccgtgtt | 5880 |
| tcaatcttcc | aggacagacg | ttatgctgga | agtcagttga | acgagcgtgg ttcgatctcg | 5940 |
| aacatgtcta | gctcgaacta | ttctgggtcg | agattagcaa | gatcaccaac caatgcctcc | 6000 |
| accaattcat | caaactcatc | gatgaaccga | tcaggaagat | cttcgggata cccatcaagc | 6060 |
| aacatccagc | ctggttattc | ggggattgtt | ggtacctcc |  | 6099 |

<210> SEQ ID NO 30
<211> LENGTH: 20
<212> TYPE: DNA
<213> ORGANISM: Artificial Sequence
<220> FEATURE:
<223> OTHER INFORMATION: primer HR-F

<400> SEQUENCE: 30
tcatgatagc catcggccac                      20

```
<210> SEQ ID NO 31
<211> LENGTH: 20
<212> TYPE: DNA
<213> ORGANISM: Artificial Sequence
<220> FEATURE:
<223> OTHER INFORMATION: primer HR-R

<400> SEQUENCE: 31
ccaccaacca gccccattat                                              20
```

LONG-CHAIN DIBASIC ACID WITH LOW CONTENT OF HYDROXYL ACID IMPURITY AND PRODUCTION METHOD THEREOF

CROSS-REFERENCE TO RELATED APPLICATIONS

This application claims priority to and the benefit of Chinese Patent Application No. 201810734180.4, filed on Jul. 6, 2018 and Chinese Patent Application No. 201810734353.2 filed on Jul. 6, 2018, and Chinese Patent Application No. 201910321631.6, filed on Apr. 22, 2019, the disclosures of which are incorporated herein by reference in their entirety.

SEQUENCE STATEMENT

Incorporated by reference herein in its entirety is the Sequence Listing entitled "NI2018TC410US_ sequence_ listing," created Jul. 6, 2018, size of 33 kilobytes.

TECHNICAL FIELD

The present invention relates to a long-chain dibasic acid with low content of hydroxyl acid impurity and a production method thereof, and relates to a method for producing a long-chain dibasic acid with low content of hydroxyl acid impurity by utilizing a long-chain dibasic acid producing strain prepared by a homologous recombination method.

BACKGROUND ART

Long-chain dibasic acid (LCDA; also known as long-chain dicarboxylic acid or long-chain diacid) includes a dibasic acid of the chemical formula $HOOC(CH_2)_nCOOH$, where $n \geq 7$. As an important monomer raw material, long-chain dibasic acid is widely used in the synthesis of nylon, resins, hot melt adhesives, powder coatings, preservatives, perfumes, lubricants, plasticizers and the like.

For a long time, long-chain dibasic acid is synthesized from petroleum through conventional chemical synthesis pathways, for example, from butadiene by a multi-step oxidation process. However, the chemical synthesis method faces various challenges. Dibasic acid obtained by the chemical synthesis method is a mixture of long-chain dibasic acid and short-chain dibasic acid. Therefore, complex subsequent extraction and purification steps are required, which are huge obstacles for production process and production cost. Due to its low pollution, environmental friendliness, and the ability to synthesize products that are difficult to be synthesized by chemical synthesis method, such as a long-chain dibasic acid having 12 or more carbon atoms, and high purity and other characteristics, the production of a long-chain dibasic acid by microbiological fermentation techniques have obvious advantages over traditional chemical synthesis method.

Previously, the improvement of a dibasic acid producing strain was mostly achieved by traditional random mutagenesis or genetic engineering methods. Due to the randomness of mutagenesis itself, there is a high requirement for screening throughput, and each time a new round of mutagenesis screening is required for changed trait, which has become an important limiting factor in technology. Genetic engineering method can be used for targeted genetic modification of a strain to obtain a superior strain with higher yield. The production method of a long-chain dibasic acid by microbiological fermentation method is mainly on the ω-oxidation of alkane, which can then be degraded by the β-oxidation pathway. Although the purity of a dibasic acid produced by the fermentation method is higher than that of the conventional chemical method, some impurity acids may also be produced. The presence of the impurity acids may cause many challenges in the subsequent extraction and purification processes, especially in the treatment stages such as sterilization and filtration, etc. It is difficult to effectively separate a long-chain dibasic acid from other impurities, which greatly reduces production efficiency and product yield. The problems in the quality of a long-chain dibasic acid product or crude product caused by the presence of impurities bring great troubles to downstream customers. Therefore, reducing the content of impurity acids has become an important problem for biosynthesis process, which has affected the development of long-chain dibasic acid industry by biological methods to some extent.

Previous studies have shown that the yield of a long-chain dibasic acid can be increased by enhancing the ω-oxidation pathway and inhibiting the β-oxidation pathway. For example, Pictaggio et al. of Coginis company (Mol. Cell. Biol., 11(9), 4333-4339, 1991) reported that knocking out two alleles of each POX4 and POX5 can effectively block the β-oxidation pathway, thereby achieving a substrate conversion efficiency of 100%. Further overexpression of the genes of the two key enzymes, P450 and oxidoreductase CPR-a, in the rate-limiting step of the ω-oxidation pathway can effectively increase yield. Lai Xiaoqin et al. (Chinese patent CN103992959B) reported that the introduction of one copy of CYP52A14 gene into a dibasic acid-producing strain can also effectively increase the conversion rate and production efficiency of dibasic acids. In addition, Cao Zhuan et al. from Tsinghua University (Biotechnol. J., 1, 68-74, 2006) found that knocking out one copy of the key gene CAT in the transportation process of acyl-CoA from peroxysome to mitochondrion, thereby partially blocking the acyl-CoA from entering the citric acid cycle, which also can effectively reduce the degradation of dibasic acid, thereby significantly increasing the yield of dibasic acid.

However, there have been no reports of studies using genetic engineering methods to modify a dibasic acid-producing strain to reduce the content of hydroxyl acids. There is still a need in the art for a long-chain dibasic acid product with low content of impurities, as well as a strain that produces such product by fermentation, and preparation method thereof.

SUMMARY OF THE INVENTION

The present invention relates to a recombinant long-chain dibasic acid producing microorganism, having increased alcohol dehydrogenase (EC 1.1.1.1) activity and optionally decreased acyl-CoA oxidase (EC 1.3.3.6) activity.

In some embodiments, the recombinant long-chain dibasic acid producing microorganism contains an overexpressed ADH gene or its homologous gene.

In some embodiments, POX4 gene or its homologous gene is attenuated, e.g. inhibited or inactivated, in the recombinant long-chain dibasic acid producing microorganism.

In some embodiments, in the recombinant long-chain dibasic acid producing microorganism, POX4 gene or its homologous gene is replaced with ADH gene or its homologous gene, e.g. one copy of POX4 gene or its homologous gene in the recombinant long-chain dibasic acid producing microorganism is replaced with one copy of ADH gene or its homologous gene.

The present invention further relates to a method of producing a long-chain dibasic acid by using the recombinant long-chain dibasic acid producing microorganism, comprising culturing the recombinant long-chain dibasic acid producing microorganism under conditions suitable to the growth of the recombinant long-chain dibasic acid producing microorganism, and optionally isolating, extracting and/or purifying the long-chain dibasic acid from the culture.

The present invention further relates to a method of producing a long-chain dibasic acid, comprising culturing the recombinant long-chain dibasic acid producing microorganism according to the invention, and optionally isolating, extracting and/or purifying the long-chain dibasic acid.

In some embodiments, the content of hydroxyl acid impurity is significantly reduced in a long-chain dibasic acid produced by the recombinant long-chain dibasic acid producing microorganism according to the invention, e.g. relative to that in the long-chain dibasic acid produced by a microorganism having no increased alcohol dehydrogenase activity (such as having no overexpressed ADH gene) and/or optionally having no decreased acyl-CoA oxidase activity (such as having no attenuated POX4 gene), such as wild type or starting microorganism.

In some embodiments, the content of hydroxyl acid impurity is significantly reduced in a long-chain dibasic acid produced by the recombinant long-chain dibasic acid producing microorganism according to the invention, e.g. relative to that in the long-chain dibasic acid produced by a microorganism in which POX4 gene is not replaced, e.g. with ADH gene.

In some embodiments, the recombinant long-chain dibasic acid producing microorganism is selected from the group consisting of *Corynebacterium, Geotrichum candidum, Candida, Pichia, Rhodotroula, Saccharomyces* and *Yarrowia*, more preferably the microorganism is yeast, and more preferably the microorganism is *Candida tropicalis* or *Candida sake*.

In some embodiments, the long-chain dibasic acid is selected from C9 to C22 long-chain dibasic acids, preferably selected from C9 to C18 long-chain dibasic acids, more preferably one or more selected from the group consisting of C10 dibasic acid, C11 dibasic acid, C12 dibasic acid, C13 dibasic acid, C14 dibasic acid, C15 dibasic acid and C16 dibasic acid. More preferably, the long-chain dibasic acid is at least one or more of C10 to C16 dibasic acids, or at least one or more of n-C10 to C16 dibasic acids, e.g. at least one or more selected from the group consisting of sebacic acid, undecanedioic acid, dodecanedioic acid, tridecanedioic acid, tetradecanedioic acid, pentadecanedioic acid and hexadecanedioic acid.

In some embodiments, the hydroxyl acid impurity comprises a hydroxyl fatty acid having one carboxyl group —COOH.

In some embodiments, the hydroxyl fatty acid has one terminal carboxyl group and one terminal hydroxyl group.

In some embodiments, the hydroxyl fatty acid has a chemical formula of $CH_2OH—(CH_2)_n—COOH$, where $n \geq 7$.

In some embodiments, the hydroxyl fatty acid includes any one or more of a hydroxyl fatty acid having 9 carbon atoms, a hydroxyl fatty acid having 10 carbon atoms, a hydroxyl fatty acid having 11 carbon atoms, a hydroxyl fatty acid having 12 carbon atoms, a hydroxyl fatty acid having 13 carbon atoms, a hydroxyl fatty acid having 14 carbon atoms, a hydroxyl fatty acid having 15 carbon atoms, a hydroxyl fatty acid having 16 carbon atoms, a hydroxyl fatty acid having 17 carbon atoms, a hydroxyl fatty acid having 18 carbon atoms, and a hydroxyl fatty acid having 19 carbon atoms.

In some embodiments, in the production of a long-chain dibasic acid by fermentation of a recombinant long-chain dibasic acid producing microorganism having increased alcohol dehydrogenase activity and optionally decreased acyl-CoA oxidase activity according to the invention, the content of hydroxyl acid impurity in the fermentation broth after completion of fermentation is reduced by at least 10%, preferably at least 20%, more preferably at least 30%, 40%, 50%, 60%, 70%, 80%, 90%, 95%, 96%, 97%, 98%, 99% or more, relative to a microorganism having no increased alcohol dehydrogenase activity and/or having no decreased acyl-CoA oxidase activity.

In some embodiments, in the production of a long-chain dibasic acid by fermentation of a recombinant long-chain dibasic acid producing microorganism according to the invention (e.g. in which POX4 gene or its homologous gene is replaced with ADH gene or its homologous gene), the content of hydroxyl acid impurity in the fermentation broth after completion of fermentation is reduced by at least 10%, preferably at least 20%, more preferably at least 30%, 40%, 50%, 60%, 70%, 80%, 90%, 95%, 96%, 97%, 98%, 99% or more, relative to a microorganism in which POX4 gene or its homologous gene is not replaced, e.g. with ADH gene or its homologous gene.

In some embodiments, in the production of a long-chain dibasic acid produced by the recombinant long-chain dibasic acid producing microorganism according to the invention, the fermentation broth after completion of fermentation contains hydroxyl acid impurity with a content of below 3%, wherein the percentage is the mass percentage of the hydroxyl acid impurity to the long-chain dibasic acid in the fermentation broth.

In some embodiments, a long-chain dibasic acid produced by fermentation of a recombinant long-chain dibasic acid producing microorganism according to the invention contains hydroxyl fatty acid impurity, the content of which is below 10,000 ppm, preferably below 8,000 ppm, 4,000 ppm, 2,000 ppm, 300 ppm, 250 ppm, 200 ppm, 150 ppm or lower.

In some embodiments, when the long-chain dibasic acid to be produced by fermentation is C12 dibasic acid e.g. dodecanedioic acid, the hydroxyl fatty acid impurity is mainly a hydroxyl fatty acid having 12 carbon atoms, and the content of the hydroxyl fatty acid impurity having 12 carbon atoms is less than 4,000 ppm.

In some embodiments, when the long-chain dibasic acid to be produced by fermentation is C10 dibasic acid e.g. decanedioic acid, the hydroxyl fatty acid impurity is mainly a hydroxyl fatty acid having 10 carbon atoms, and the content of the hydroxyl fatty acid impurity having 10 carbon atoms is less than 2,000 ppm.

In some embodiments, when the long-chain dibasic acid to be produced by fermentation is C16 dibasic acid e.g. hexadecanedioic acid, the hydroxyl fatty acid impurity is mainly a hydroxyl fatty acid having 16 carbon atoms, and the content of the hydroxyl fatty acid impurity having 16 carbon atoms is less than 9,000 ppm.

The present invention further relates to a method of modifying a long-chain dibasic acid producing microorganism, comprising enhancing alcohol dehydrogenase activity and optionally decreasing acyl-CoA oxidase activity.

In some embodiments, the method of modifying a long-chain dibasic acid producing microorganism according to the invention comprises replacing POX4 gene or its homologous gene in the genome of the long-chain dibasic acid producing microorganism with ADH gene or its homologous gene, preferably by homologous recombination.

In some embodiments, the content of hydroxyl acid impurity in a long-chain dibasic acid produced by a modified long-chain dibasic acid producing microorganism according to the invention is significantly reduced, relative to the microorganism before modified, e.g. in which POX4 gene is not replaced, e.g. with ADH gene.

The present invention also relates to a long-chain dibasic acid with low content of hydroxyl acid impurity, wherein the content of hydroxyl acid impurity in the long-chain dibasic acid is more than 0 and less than 10,000 ppm, preferably less than 4,000 ppm, more preferably less than 300 ppm, and the hydroxyl acid impurity comprises a hydroxyl fatty acid having one carboxyl group.

In some embodiments, the long-chain dibasic acid is selected from the group consisting of C9-C22 long-chain dibasic acids, preferably selected from the group consisting of C9-C18 long-chain dibasic acids, and more preferably one or more of C10 dibasic acid, C11 dibasic acid, C12 dibasic acid, C13 dibasic acid, C14 dibasic acid, C15 dibasic acid and C16 dibasic acid. Preferably, the long-chain dibasic acid is at least one or more of C10 to C16 dibasic acids, or at least one or more of n-C10 to C16 dibasic acids, preferably at least one selected from the group consisting of sebacic acid, undecanedioic acid, dodecanedioic acid, tridecanedioic acid, tetradecanedioic acid, pentadecanedioic acid and hexadecanedioic acid.

In some embodiments, the hydroxyl fatty acid has one terminal carboxyl group and one terminal hydroxyl group, and the hydroxyl fatty acid has a chemical formula of $CH_2OH—(CH_2)_n—COOH$, where $n \geq 7$.

Preferably, the hydroxyl acid impurity includes any one of a hydroxyl fatty acid having 9 carbon atoms, a hydroxyl fatty acid having 10 carbon atoms, a hydroxyl fatty acid having 11 carbon atoms, a hydroxyl fatty acid having 12 carbon atoms, a hydroxyl fatty acid having 13 carbon atoms, a hydroxyl fatty acid having 14 carbon atoms, a hydroxyl fatty acid having 15 carbon atoms, a hydroxyl fatty acid having 16 carbon atoms, a hydroxyl fatty acid having 17 carbon atoms, a hydroxyl fatty acid having 18 carbon atoms, and a hydroxyl fatty acid having 19 carbon atoms.

In some embodiments, when the long-chain dibasic acid is C12 dibasic acid e.g. dodecanedioic acid, the hydroxyl acid impurity is mainly a hydroxyl fatty acid having 12 carbon atoms, and the content of the hydroxyl fatty acid impurity having 12 carbon atoms is less than 4,000 ppm, preferably less than 3,000 ppm, 2,000 ppm, 1,000 ppm, 500 ppm, 300 ppm, 200 ppm, 150 ppm or less.

In some embodiments, when the long-chain dibasic acid is C10 dibasic acid e.g. decanedioic acid, the hydroxyl acid impurity is mainly a hydroxyl fatty acid having 10 carbon atoms, and the content of the hydroxyl fatty acid impurity having 10 carbon atoms is less than 2,000 ppm, preferably less than 1,500 ppm, 1,000 ppm, 500 ppm, 300 ppm, 200 ppm, 150 ppm or less.

In some embodiments, when the long-chain dibasic acid is C16 dibasic acid e.g. hexadecanedioic acid, the hydroxyl acid impurity is mainly a hydroxyl fatty acid having 16 carbon atoms, and the content of the hydroxyl fatty acid impurity having 16 carbon atoms is less than 9,000 ppm, preferably less than 8,000 ppm, 6,000 ppm, 3,000 ppm, 2,000 ppm, 1,000 ppm, 800 ppm, 600 ppm, 500 ppm, 400 ppm, 300 ppm, 200 ppm or less.

In some embodiments, one copy of POX4 gene or a homologous gene thereof in the genome of a long-chain dibasic acid producing microorganism is replaced with one copy of ADH gene or a homologous gene thereof.

The present invention further relates to a fermentation broth in a process of producing a long-chain dibasic acid by fermentation with a microorganism, wherein the fermentation broth contains hydroxyl acid impurity, and the content of the hydroxyl acid impurity is less than 3%, less than 2%, less than 1.5%, less than 1.3%, such as less than 1.2%, 1.1%, 1.0%, 0.9%, 0.8%, 0.7%, 0.6%, 0.5%, 0.4%, 0.3% or less, wherein the percentage is the mass percentage of the hydroxyl acid impurity to the long-chain dibasic acid in the fermentation broth.

Preferably, the long-chain dibasic acid is selected from C9-C22 long-chain dibasic acids, and the hydroxyl acid impurity is a hydroxyl fatty acid having one terminal carboxyl group and one terminal hydroxyl group.

The present invention further relates to a method of producing a long-chain dibasic acid according to the invention, comprising obtaining a modified long-chain dibasic acid producing microorganism in which the POX4 gene or a homologous gene thereof in the genome of the long-chain dibasic acid producing microorganism is replaced with the ADH gene or a homologous gene thereof; culturing the modified long-chain dibasic acid producing microorganism to produce the long-chain dibasic acid by fermentation; optionally, further comprising separating, extracting and/or purifying the long-chain dibasic acid from the culture product.

Preferably, one copy of the POX4 gene or homologous gene thereof in the genome of the modified long-chain dibasic acid producing microorganism is replaced with one copy of the ADH gene or homologous gene thereof.

Preferably, the replacement is carried out by homologous recombination.

In some embodiments, the microorganism is yeast; and more preferably, the microorganism is selected from the group consisting of *Candida tropicalis* and *Candida sake*.

The present invention further relates to a product obtained by the method of producing a long-chain dibasic acid.

In some embodiments, the long-chain dibasic acid is selected from the group consisting of C9-C22 long-chain dibasic acids; and the hydroxyl acid impurity comprises a hydroxyl fatty acid having one carboxyl group (—COOH).

In other words, the present invention provides a novel long-chain dibasic acid with low content of hydroxyl acid impurity, and provides a novel method of preparing a dibasic acid-producing strain, a strain, and a method of producing a long-chain dibasic acid by fermentation so as to solve the technical problem that impurity acid such as hydroxyl acid is produced in a biological production process of a long-chain dibasic acid.

Preferably, in the present invention, one copy of ADH gene is added to the genome of a dibasic acid-producing strain by homologous recombination method, and the nucleotide sequence thereof is set forth in SEQ ID NO.3.

Preferably, the method of preparing a dibasic acid-producing strain of the present invention comprises: (1) preparing a homologous recombination template, comprising recombinant templates upstream and downstream of a target site, the ADH gene and a resistance marker gene HYG (hygromycin resistance gene), and then obtaining a complete recombinant template by PCR overlap extension method; (2) transforming competent cells with the complete recombinant template, and screening out a strain containing the resistance marker on a resistance culture medium containing hygromycin; and (3) removing the resistance marker gene contained at the target site by further homologous recombination, i.e. obtaining a producer strain in which only the ADH gene is contained at the target site.

After further removing the resistance marker from the mutant strain, the mass ratio of the hydroxyl acid impurity in the fermentation broth after completion of fermentation is significantly decreased compared with the parent strain, and the content of the hydroxyl acid impurity in the final long-chain dibasic acid product obtained after extraction and purification of the fermentation broth can be reduced to be less than 200 ppm, thereby further improving the purity of the fermentation product long-chain dibasic acid, making the dibasic acid product which are used as an important raw material for engineering plastics, synthetic perfumes, cold-resistant plasticizers, high-grade lubricating oils and polyamide hot melt adhesives and other products, more conducive to the production of and the quality improvement of the downstream products. A long-chain dibasic acid product with low content of hydroxyl acid impurity has better light transmittance in preparing nylon filament, and is more suitably applied in the field of products with high requirements for light transmission of nylon. More importantly, a long-chain dibasic acid with low content of hydroxyl acid impurity greatly reduces difficulties in the subsequent processes of extraction and purification of the dibasic acid and wastewater treatment, simplifies the processes and saves energy.

BRIEF DESCRIPTION OF THE DRAWINGS

FIG. 1 is a schematic diagram showing the replacement of gene POX4 with gene ADH and removal of the hygromycin resistance marker by homologous recombination.

DETAILED DESCRIPTION OF THE INVENTION

Definition

Unless defined otherwise, technical and scientific terms used herein have the same meanings as commonly understood by skilled persons in the art. See e.g. Singleton et al., DICTIONARY OF MICROBIOLOGY AND MOLECULAR BIOLOGY $2^{nd}$ ed., J. Wiley & Sons (New York, N.Y. 1994); Sambrook et al., MOLECULAR CLONING, A LABORATORY MANUAL, Cold Springs Harbor Press (Cold Springs Harbor, 1989).

Long-chain alkane: the fermentation substrate of the present invention includes a long-chain alkane, which belongs to saturated chain hydrocarbons, and is a saturated hydrocarbon in hydrocarbons and its whole structure is mostly composed of carbon, hydrogen, carbon-carbon single bond and carbon-hydrogen single bond merely, comprising an alkane having a chemical formula of $CH_3(CH_2)_nCH_3$, where $n \geq 7$. Preferred are C9-C22 n-alkanes, more preferred are C9-C18 n-alkanes, and most preferred are C10, C11, C12, C13, C14, C15 or C16 n-alkane.

Long-chain dibasic acid (LCDA; also known as long-chain dicarboxylic acid or long-chain diacid, or abbreviated as dibasic acid hereinafter) includes a dibasic acid with a chemical formula of $HOOC(CH_2)_nCOOH$, where $n \geq 7$. Preferably, the long-chain dibasic acid is selected from the group consisting of C9-C22 long-chain dibasic acids, preferably selected from the group consisting of C9-C18 long-chain dibasic acids, and more preferably comprises one or more of C10 dibasic acid, C11 dibasic acid, C12 dibasic acid, C13 dibasic acid, C14 dibasic acid, C15 dibasic acid and C16 dibasic acid. Preferably, the long-chain dibasic acid is at least one or more of C10 to C16 dibasic acids, and preferably at least one or more of n-C10 to C16 dibasic acids, preferably at least one or more selected from the group consisting of sebacic acid, undecanedioic acid, dodecanedioic acid, tridecanedioic acid, tetradecanedioic acid, pentadecanedioic acid and hexadecanedioic acid.

Long-chain dibasic acid-producing microorganism: a strain, such as bacterium, yeast, mold and the like, which has been reported to be capable of producing and accumulating a dibasic acid, such as *Corynebacterium, Geotrichum candidum, Candida, Pichia, Rhodotroula, Saccharomyces, Yarrowia* and the like. Many species of the *Candida* are excellent strains for producing a dibasic acid by fermentation. The strain for fermentation preferably includes: *Candida tropicalis* or *Candida sake*. In a particular embodiment, the microorganism is CCTCC M2011192 or CCTCC M203052.

The POX4 gene (GenBank Accession No.: M12160) encodes an acyl-CoA oxidase (EC 1.3.3.6) involved in the oxidation process of fatty acids and their derivatives in the β-oxidation pathway. It is known that there are three PDX genes in *Candida tropicalis*, POX2, POX4 and POX5, which may together participate in the β-oxidation pathway in the form of an octamer.

The ADH gene encodes an ethanol dehydrogenase (EC 1.1.1.1), which is widely found in most organisms, catalyzes the oxidation of alcohols to aldehydes or ketones with the help of $NAD^+$ coenzyme, and also catalyzes the reverse process in plants, yeasts, and some bacteria to ensure an adequate supply of $NAD^+$ in cells. The ADH in *Candida tropicalis* participates in the oxidation process of alcohol to aldehyde in the ω-oxidation pathway.

The hydroxyl acid impurity of the present invention comprises a hydroxyl fatty acid containing one carboxyl group (—COOH). Preferably, the hydroxyl fatty acid has one terminal carboxyl group and one terminal hydroxyl group, and the hydroxyl fatty acid has a chemical formula of $CH_2OH$—$(CH_2)_n$—$COOH$, wherein $n \geq 7$. Preferably, the hydroxyl acid impurity comprises a long-chain hydroxyl fatty acid having 9 or more carbon atoms in the carbon chain and simultaneously one terminal carboxyl group and one hydroxyl group, such as any one of a hydroxyl fatty acid having 9 carbon atoms, a hydroxyl fatty acid having 10 carbon atoms, a hydroxyl fatty acid having 11 carbon atoms, a hydroxyl fatty acid having 12 carbon atoms, a hydroxyl fatty acid having 13 carbon atoms, a hydroxyl fatty acid having 14 carbon atoms, a hydroxyl fatty acid having 15 carbon atoms, a hydroxyl fatty acid having 16 carbon atoms, a hydroxyl fatty acid having 17 carbon atoms, a hydroxyl fatty acid having 18 carbon atoms, and a hydroxyl fatty acid having 19 carbon atoms. The hydroxyl fatty acid having 9 carbon atoms refers to a long-chain hydroxyl fatty acid having 9 carbon atoms and having one terminal carboxyl group and one terminal hydroxyl group.

The hydroxyl acid impurity corresponds to the long-chain dibasic acid to be produced, that is, the hydroxyl acid impurity has the same number of carbon atoms as the long chain dibasic acid, but has one carboxyl group and one hydroxyl group. In the present invention, the terms hydroxyl acid and hydroxyl fatty acid can be used interchangeably.

When a long-chain dibasic acid is produced by fermentation with a microorganism having increased alcohol dehydrogenase activity and optionally decreased acyl-CoA oxidase activity according to the invention (e.g. POX4 gene or its homologous gene is replaced with ADH gene or its homologous gene), the content of hydroxyl acid impurity in the fermentation broth after completion of fermentation is significantly reduced, such as by at least 5%, 6%, 7%, 8%, 9%, 10%, 12%, 14%, 16%, 18%, 20%, 25%, 30%, 35%, 40%, 50%, 60%, 70%, 80%, 90%, 95% or more, relative to a microorganism having no increased alcohol dehydrogenase activity and/or having no decreased acyl-CoA oxidase activity (e.g. POX4 gene or its homologous gene is not replaced with ADH gene or its homologous gene).

As used herein, the "increased activity" of an enzyme refers to that compared to the reference, the enzymatic activity is increased by at least 5%, 10%, 20%, 30%, 40%, 50%, 60%, 70%, 80%, 90%, 100%, 150%, 200%, 250%, 300% or more.

As used herein, the "decreased activity" of an enzyme refers to that compared to the reference, the enzymatic activity is decreased by at least 5%, 10%, 20%, 30%, 40%, 50%, 60%, 70%, 80%, 90%, 95%, 99% or more, even 100%.

Many methods for increasing activity of an enzyme are known in the art, e.g. include but not limited to, overexpression of an enzyme coding gene, such as using a strong promoter, increasing gene copy number and so on.

Many methods for decreasing activity of an enzyme are known in the art, e.g. include but not limited to, attenuation or inactivation of an enzyme coding gene, such as deleting or knocking out partial or complete enzyme coding gene, using a weak promoter, using an antagonist or inhibitor such as antibody, interference RNA etc.

In the context of the invention, the reference may be a wild type microorganism or the same microorganism before the desired genetic manipulation is performed, e.g. the starting microorganism to be genetically manipulated to increase enzyme activity. In the context of the invention, the parent microorganism and the starting microorganism can be used interchangeably, and refers to the microorganism to which the desired genetic manipulation (e.g. to increase or decrease enzyme activity) is performed.

As used herein, the "overexpression" refers to the expression level of a gene, compared to the level before genetic manipulation is performed, is increased, e.g. by at least 5%, 10%, 20%, 30%, 40%, 50%, 60%, 70%, 80%, 90%, 100%, 150%, 200%, 250%, 300% or more. The methods for overexpressing a gene are known in the art, including but not limited to, using a strong promoter, increasing copy number of a gene and so on. The copy number of a gene can be increased by e.g. introducing one or more copies of an exogenous or endogenous gene, e.g. by an expression vector or integrated into the genome.

As used herein, the "exogenous gene" refers to a gene derived from another cell or organism, e.g. a gene from the same or different species.

As used herein, the "endogenous gene" refers to a gene from the cell or organism itself.

In some embodiments, in the recombinant long-chain dibasic acid producing microorganism according to the invention, one or more copies of ADH gene or its homologous gene can be integrated into the genome, e.g. by means of homologous recombination, optionally at any site in the genome, e.g. one copy of any gene in the genome is replaced with one or more copies of ADH gene or its homologous gene.

When a long-chain dibasic acid is produced by fermentation in the present invention, the fermentation broth after completion of fermentation contains hydroxyl acid impurity, and the content of the hydroxyl acid impurity is significantly decreased, such as at least 5%, 6%, 7%, 8%, 9%, 10%, 12%, 14%, 16%, 18%, 20%, 25%, 30%, 35%, 40%, 50%, 60%, 70%, 80%, 90%, 95% or more, relative to a microorganism in which the POX4 gene or homologous gene thereof is not replaced.

In some embodiments, a long-chain dibasic acid is produced by fermentation with a microorganism, and the fermentation broth contains hydroxyl fatty acid impurity, wherein the content of the hydroxyl fatty acid impurity is reduced to less than 3%, less than 2%, less than 1.5%, less than 1.3%, such as less than 1.2%, 1.1%, 1.0%, 0.9%, 0.8%, 0.7%, 0.6%, 0.5%, 0.4%, 0.3% or less, and the percentage is the mass percentage of the hydroxyl fatty acid impurity to the long chain dibasic acid in the fermentation broth.

In some embodiments, the long-chain dibasic acid produced by fermentation contains hydroxyl fatty acid impurity, and the content of the hydroxyl fatty acid impurity is reduced to less than 10,000 ppm, such as less than 8,000 ppm, 4,000 ppm, 2,000 ppm, 300 ppm, 250 ppm, 200 ppm, 150 ppm or less.

In the present invention, the unit of the impurity content, ppm, is the mass ratio of the impurity to the long-chain dibasic acid, and 100 ppm=$100*10^{-6}$=0.01%.

In one embodiment of the present invention, when C12 long-chain dibasic acid e.g. dodecanedioic acid is produced by fermentation with a microorganism according to the present invention, the hydroxyl acid impurity is mainly a hydroxyl fatty acid having 12 carbon atoms, and the content of the hydroxyl fatty acid impurity having 12 carbon atoms is less than 4,000 ppm, preferably less than 3,000 ppm, 2,000 ppm, 1,000 ppm, 500 ppm, 300 ppm, 200 ppm, 150 ppm or less. The hydroxyl fatty acid having 12 carbon atoms has a chemical formula of $CH_2OH-(CH_2)_{10}-COOH$.

In one embodiment of the present invention, when C10 long-chain dibasic acid e.g. decanedioic acid is produced by fermentation with a microorganism according to the present invention, the hydroxyl acid impurity is mainly a hydroxyl fatty acid having 10 carbon atoms, and the content of the hydroxyl fatty acid impurity having 10 carbon atoms is less than 2,000 ppm, preferably less than 1,500 ppm, 1,000 ppm, 500 ppm, 300 ppm, 200 ppm, 150 ppm or less. The hydroxyl fatty acid having 10 carbon atoms has a chemical formula of $CH_2OH-(CH_2)_8-COOH$.

In one embodiment of the present invention, when C16 long-chain dibasic acid e.g. hexadecanedioic acid is produced by fermentation with a microorganism according to the present invention, the hydroxyl acid impurity is mainly a hydroxyl fatty acid having 16 carbon atoms, and the content of the hydroxyl fatty acid impurity having 16 carbon atoms is less than 9,000 ppm, preferably less than 8,000 ppm, 6,000 ppm, 3,000 ppm, 2,000 ppm, 1,000 ppm, 800 ppm, 600 ppm, 500 ppm, 400 ppm, 300 ppm, 200 ppm or less. The hydroxyl fatty acid impurity having 16 carbon atoms has a chemical formula of $CH_2OH-(CH_2)_{14}-COOH$.

The detection of the content of the dibasic acid and impurity can be carried out by a technique well known to those skilled in the art, such as an internal standard method or a normalization method and the like of gas chromatography detection method.

Homologous genes refer to two or more gene sequences with a sequence similarity of up to 80%, including orthologous genes, paralogous genes and/or xenologous genes. The homologous gene of the POX4 gene or the ADH gene referred in the present invention can be an orthologous gene of the POX4 gene or the ADH gene, or a paralogous gene or a xenologous gene thereof.

Sequence identity refers to the percentage of the residues of a polynucleotide sequence variant that are identical to a non-variant sequence after sequence alignment and introduction of a gap. In a specific embodiment, the polynucleotide variant has at least about 70%, at least about 75%, at least about 80%, at least about 90%, at least about 95%, at least about 96%, at least about 97%, at least about 98%, at least about 99%, at least about 99.1%, at least about 99.2%, at least about 99.3%, 99.4%, at least about 99.5%, at least about 99.6%, 99.7%, at least about 99.8%, at least about 99.9%, at least about 99.91%, at least about 99.92%, at least about 99.93%, at least about 99.94%, at least about 99.95%, or at least about 99.96% polynucleotide homology to the polynucleotide described herein.

As used herein, the terms "homology" and "identity" are used interchangeably herein to refer to the extent of non-variance of nucleotide sequences, which can be detected through the number of identical nucleotide bases by aligning a polynucleotide with a reference polynucleotide. The sequence identity can be determined by standard alignment algorithm programs used with default gap penalties established by each supplier. Homologous nucleic acid molecules refer to a pre-determined number of identical or homologous nucleotides. Homology includes substitutions that do not change the encoded amino acid ("silent substitution") as well as identical residues. Substantially homologous nucleic acid molecules hybridize typically at moderate stringency or high stringency all along the length of the nucleic acid or along at least about 70%, 80% or 90% of the full-length nucleic acid molecule of interest. Nucleic acid molecules that contain degenerate codons in place of codons in the hybridizing nucleic acid molecule are also contemplated in the invention. Whether any two nucleic acid molecules have nucleotide sequences that are at least 80%, 85%, 90%, 95%, 96%, 97%, 98% or 99% "identical" can be determined using a known computer algorithm such as the BLASTN, FASTA, DNAStar and Gap (University of Wisconsin Genetics Computer Group (UWG), Madison Wis., USA). Percent homology or identity of nucleic acid molecules can be determined, e.g. by comparing sequence information using a GAP computer program (e.g., Needleman et al. J. Mol. Biol. 48: 443 (1970), as revised by Smith and Waterman (Adv. Appl. Math. 2: 482 (1981)). Briefly, a GAP program defines similarity as the number of aligned symbols (i.e., nucleotides) which are similar, divided by the total number of symbols in the shorter of the two sequences.

PCR overlap extension, also known as SOE (gene splicing by overlap extension) PCR, refers to a method of splicing different DNA fragments together through PCR amplification by designing primers having complementary ends.

Homologous recombination refers to a recombination between DNA molecules depending on sequence similarity, and is most commonly found within cells for repairing mutations generated during mitosis. Homologous recombination technology has been widely used in genome editing, including gene knockout, gene repair, and introduction of a new gene to a specific site, etc. A class of microorganisms represented by Saccharomyces cerevisiae has a high probability of homologous recombination in cells, which does not depend on sequence specificity, and has obvious advantages in genome editing. While site-specific recombination, depending on the involvement of specific site and site-specific recombinase, occurs only between specific sites, such as Cre/loxP, FLP/FRT, and the like. The homologous recombination technique used in this patent does not belong to site-specific recombination, and the recombination depends on the intracellular DNA repair system.

Resistance marker refers to one of selectable markers that often have the ability to confer a transformant survival in the presence of an antibiotic. The resistance marker gene includes NPT, HYG, BLA, CAT, etc., which can be resistant to kanamycin, hygromycin, ampicillin/carbenicillin, and chloramphenicol, etc., respectively. Preferably, the resistance marker gene is hygromycin resistance gene HYG.

During fermentation, the fermentation medium comprises: a carbon source, a nitrogen source, an inorganic salt, and a nutritional factor.

In some embodiments, the carbon source includes one or more selected from the group consisting of glucose, sucrose, and maltose; and/or the carbon source is added in an amount of 1% to 10% (w/v), such as 1.5%, 2.0%, 2.5%, 3.0%, 3.5%, 4.0%, 4.5%, 5.0%, 6.0%, 7.0%, 8.0%, or 9.0%.

In some embodiments, the nitrogen source includes one or more selected from the group consisting of peptone, yeast extract, corn syrup, ammonium sulfate, urea, and potassium nitrate; and/or the nitrogen source is added in a total amount of 0.1% to 3% (w/v), such as 0.2%, 0.4%, 0.5%, 0.6%, 0.8%, 1.0%, 1.2%, 1.5%, 1.8%, 2.0%, or 2.5%.

In some embodiments, the inorganic salt includes one or more selected from the group consisting of monopotassium phosphate, potassium chloride, magnesium sulfate, calcium chloride, iron chloride, and copper sulfate; and/or the inorganic salt is added in a total amount of 0.1% to 1.5% (w/v), such as 0.2%, 0.3%, 0.4%, 0.5%, 0.6%, 0.7%, 0.8%, 0.9%, 1.0%, 1.1%, 1.2%, 1.3%, or 1.4%.

In some embodiments, the nutritional factor includes one or more selected from the group consisting of vitamin B1, vitamin B2, vitamin C, and biotin; and/or the nutritional factor is added in a total amount of 0 to 1% (w/v), such as 0.2%, 0.3%, 0.4%, 0.5%, 0.6%, 0.7%, 0.8%, or 0.9%. According to common knowledge in the field of fermentation, the percentage in the present invention is mass-to-volume ratio, i.e., w/v; % means g/100 mL.

The OD value of the present invention is the optical density of bacterial cells, and is a value measured with dilution by a factor of 30.

In one embodiment of the present invention, the inoculation amount of the fermentation strain is 10% to 30%, such as 11%, 12%, 13%, 14%, 15%, 16%, 17%, 18%, 19%, 20%, 22%, 24%, 25%, 27%, or 29%. When the strain is cultured until the optical density ($OD_{620}$) of bacterial cells is more than 0.5 (with dilution by a factor of 30), a substrate is added for conversion by fermentation.

Extraction and purification of long-chain dibasic acid: the fermentation broth containing a salt of a long-chain dibasic acid obtained by fermentation is subject to extraction and purification treatment to obtain a final long-chain dibasic acid product. The steps of extraction and purification include: sterilization, acidification, solid-liquid separation, and/or solvent crystallization of the fermentation broth which may contain a salt of a long-chain dibasic acid.

The extraction and purification according to the present invention may be repeated more than once, and multiple rounds of the extraction and purification steps help to further reduce the impurity content in a dibasic acid product. For example, in one embodiment of the present invention, the long-chain dodecanedioic acid product obtained by the present invention was further treated by referring to the refining process in Example 1 of the Chinese patent CN 101985416 A, and the content of the hydroxyl fatty acid impurity having 12 carbon atoms in the obtained long-chain dodecanedioic acid was reduced from more than 3,000 ppm before the treatment to less than 200 ppm, such as less than 180 ppm, less than 160 ppm, 140 ppm, 120 ppm or less.

The fermentation broth containing a salt of a long-chain dibasic acid refers to a fermentation broth containing a salt of a long-chain dibasic acid produced during a process for producing the long-chain dibasic acid by biological fermentation, and the fermentation broth containing a salt of a long-chain dibasic acid may contain sodium salt of a long-chain dibasic, potassium salt of a long-chain dibasic acid or ammonium salt of a long-chain dibasic acid, etc.

The sterilization is preferably membrane filtration: impurity such as residual bacteria and large proteins, etc. is effectively separated from the fermentation broth containing a salt of a long-chain dibasic acid by a filter membrane. Further, a ceramic membrane filtration process is preferred. When a ceramic membrane is used for membrane filtration, preferably, the pre-membrane pressure is 0.2 to 0.4 MPa; and preferably, the pore diameter of the filter membrane is 0.05 to 0.2 μm.

The acidification refers to an acidification treatment of a membrane clear liquid containing a salt of a long-chain dibasic acid obtained after membrane filtration, and the salt of the long chain dibasic acid is converted to a precipitate of the long chain dibasic acid by adding an acid. The acidification is preferably carried out using an inorganic acid such as sulfuric acid, hydrochloric acid, nitric acid, or an acid mixture thereof. The amount of the inorganic acid added during the acidification treatment needs to sufficiently precipitate the long-chain dibasic acid in the solution, and is mainly based on the end point pH of the solution. Preferably, the end point pH of acidification is less than 5, and more preferably the end point pH is less than 4.0. When an inorganic acid is added for acidification, a precipitate of a long-chain dibasic acid and a corresponding inorganic salt solution can be obtained.

The solid-liquid separation refers to separation of the obtained long-chain dibasic acid precipitate from the acidification mother liquor, which includes separation by filtration or/and centrifugation, and a commonly used solid-liquid separation apparatus can be used.

Preferably, the step of extraction and purification further includes decolorization of the fermentation broth containing a salt of a long-chain dibasic acid, comprising adding activated carbon to the fermentation broth or the membrane clear liquid containing a salt of a long-chain dibasic acid for decolorization treatment, and then removing the activated carbon by filtration after the decolorization treatment. The decolorization step can further remove impurities from the long-chain dibasic acid solution. Preferably, the activated carbon is added in an amount of 0.1 to 5 wt %, more preferably 1 to 3 wt % (relative to the amount of the long-chain dibasic acid contained in the solution).

The solvent crystallization refers to dissolving the long-chain dibasic acid precipitate in an organic solvent, and crystallizing the long-chain dibasic acid by cooling\evaporation\solvating-out, and then separating the crystals to obtain a more purified long-chain dibasic acid. The organic solvent includes one or more of alcohol, acid, ketone, and ester; wherein, the alcohol includes one or more of methanol, ethanol, isopropanol, n-propanol, and n-butanol; the acid includes acetic acid; the ketone includes acetone; and the ester includes ethyl acetate and/or butyl acetate.

In another preferred embodiment, the precipitate of a long-chain dibasic acid is dissolved in an organic solvent and then decolorized, and then is separated to obtain a clear liquid and a more purified long-chain dibasic acid. When activated carbon is used for decolorization, the decolorization temperature is 85 to 100° C., and the decolorization time is 15 to 165 min. In another preferred embodiment, after being separated, the clear liquid is subjected to cooling crystallization. The cooling crystallization may include the following steps: firstly, cooling to 65 to 80° C., incubating for 1 to 2 hours, then cooling to 25 to 35° C., and crystallizing. In another preferred embodiment, after crystallization, the resulting crystals are separated, thereby obtaining long-chain dibasic acid. The method for separating the crystals can be centrifugal separation.

In some embodiments, the present invention relates to production of nylon filaments, engineering plastics, synthetic perfumes, cold-resistant plasticizers, high-grade lubricating oils and polyamide hot melt adhesives by using the dibasic acid product obtained above.

As used herein, "optional" or "optionally" means that the subsequently described event or circumstance does or does not occur, and that the description comprises instances where the event or circumstance occurs or does not occur. For example, "optionally a step" means that the step is present or not present.

As used herein, the term "about" means a range of values including the specified value, which a person of ordinary skill in the art would consider reasonably similar to the specified value. In some embodiments, the term "about" means within a standard deviation using measurements generally acceptable in the art. In some embodiments, "about" means a range extending to +/−10% of the specified value.

The present invention will be further illustrated by the following non-limiting examples. It is well known to those skilled in the art that modifications may be made to the invention without departing from the spirit of the present invention, and such modifications are also within the scope of the present invention.

The following experimental methods are conventional methods unless otherwise specified, and the experimental materials used can be easily obtained from commercial companies unless otherwise specified.

Example 1

Medium, Culture and Fermentation Method, and Detection Method of Dibasic Acid

1. The formulation of YPD medium: 2% of peptone, 2% of glucose and 1% of yeast extract (OXOID, LP0021). For solid medium, 2% of agar powder was further needed to add.

In culturing, single colonies were taken into a 2 mL centrifuge tube containing 1 mL of YPD liquid medium, and cultured on a shaker at 30° C., 250 RPM for 1 day.

2. The formulation of seed medium: sucrose 10 to 20 g/L (specifically used 10 g/L), yeast extract 3 to 8 g/L (specifically used 3 g/L), corn syrup for industrial fermentation (referred to as corn syrup, with a total nitrogen content of 2.5 wt %) 2 to 4 g/L (specifically used 2 g/L), $KH_2PO_4$ 4 to 12 g/L (specifically used 4 g/L), urea 0.5 to 4 g/L (specifically used 0.5 g/L) (sterilized separately at 115° C. for 20 min), and a fermentation substrate of n-dodecane, n-decane, or n-hexadecane, 20 mL/L.

In culturing, a cultured bacterial solution obtained in step 1 was placed in a 500 mL shake flask containing 30 mL of the seed medium with an inoculation amount of 3-5%, and cultured on a shaker at 250 rpm, 30° C. until the $OD_{620}$ reached 0.8 (dilution by 30 folds).

3. Fermentation medium (w/v): sucrose 10 to 40 g/L (specifically used 10 g/L), corn syrup (with a total nitrogen content of 2.5 wt %) 1 to 5 g/L (specifically used 1 g/L), yeast extract 4 to 12 g/L (specifically used 4 g/L), NaCl 0 to 3 g/L (specifically not used), KNO$_3$ 4 to 12 g/L (specifically used 4 g/L), KH$_2$PO$_4$ 4 to 12 g/L (specifically used 4 g/L), urea 0.5 to 3 g/L (specifically used 0.5 g/L) (sterilized separately at 115° C. for 20 min), a fermentation substrate of n-dodecane, n-decane, or n-hexadecane, 300 to 400 mL/L (specifically used 300 mL/L), and acrylic acid 4 g/L, wherein the pH was adjusted to 7.5-7.6 with 1N HCl or 1N NaOH.

In fermentation, a seed solution obtained in step 2 was inoculated into a 500 mL shake flask containing 15 mL of the fermentation medium with an inoculation amount of 10-30%, and cultured on a shaker at 30° C., 250 rpm for 90 to 144 h. During culturing, the pH was adjusted to a set range by adding acid/base at intervals.

4. Steps for determining the yield of dibasic acid and the content of hydroxyl fatty acid impurity by gas chromatography (GC)

(1) Detection of the content of the product and impurity in the fermentation broth: the fermentation broth was subjected to conventional gas chromatography pretreatment and detected by gas chromatography. The chromatography conditions were as follows:

Chromatography column: Supelco SPB-50 30 m*0.53 mm*0.5 μm (cat. No.: 54983).

Gas chromatograph (Shimadzu, GC-2014).

Method: the initial temperature was 100° C., and the temperature was raised to 230° C. at a rate of 15° C./min, and kept for 2 min. The carrier gas was hydrogen, the inlet temperature was 280° C., the FID temperature was 280° C., and the injection volume was 4 μL.

The yield of the dibasic acid was calculated from the ratio of the peak area of the dibasic acid product to the peak area of the internal standard with known concentration, and the content of the impurity was calculated from the peak area of the dibasic acid product and the peak area of the impurity.

(2) Detection of the purity and impurity content in the solid product: the solid product was subjected to conventional gas chromatography pretreatment and detected by gas chromatography.

Chromatography conditions: chromatographic column: Supelco SPB-50 30 m*0.53 mm*0.5 μm (cat. No.: 54983).

Gas chromatograph (Shimadzu, GC-2014).

Method: the initial temperature was 100° C., and the temperature was raised to 230° C. at a rate of 15° C./min, and held for 2 min. The carrier gas was hydrogen, the inlet temperature was 280° C., the FID temperature was 280° C., and the injection volume was 4 μL.

The purity of the product and the content of the impurity were calculated from the peak area of the dibasic acid product and the peak area of the impurity.

Example 2

Preparation of Homologous Recombination Template

All DNA fragments in this example were obtained by amplification using Takara's PrimeSTAR® HS high-fidelity DNA polymerase (Takara, R040A). After electrophoresis on 1% agarose gel, the purified DNA fragment was recovered using the Axygen gel extraction kit (Axygen, AP-GX-250G).

1. Amplification of ADH gene

The genomic DNA of *Candida tropicalis* (Deposit No.: CCTCC M2011192) was extracted using Ezup yeast genomic DNA rapid extraction kit (Sangon Biotech, Cat. No. 518257), while a liquid nitrogen grounding method was also used to improve the efficiency of cell wall disruption. 5 μg of the genome was added to each 50 μL of the reaction system as a template for PCR amplification. The primers used and the PCR reaction conditions were as follows:

```
ADH-F:
                                       (SEQ ID NO. 1)
5'-CGACGGAGTTAGTGTCCGTTGTCTTGGTTGGTTTGCCAGC-3'

ADH-R:
                                       (SEQ ID NO. 2)
5'-CCATTTTCGGGTTCGCATGCAAAAACGACTGGCCGGAGAT-3'
```

Step 1: 98° C. for 30 s
Step 2: 98° C. for 10 s, 55° C. for 10 s, 72° C. for 2 m 30 s, 5 cycles
Step 3: 98° C. for 10 s, 72° C. for 2 m 30 s, 25 cycles
Step 4: 72° C. for 5 m The obtained product was designated as ADH gene and confirmed by sequencing, the sequence of which was set forth in SEQ ID NO. 3.

2. Amplification of the resistance screening marker (HYG, i.e., hygromycin resistance gene). The amplification template was the vector pCIB2 (SEQ ID NO. 4) owned by our company, and the primers' sequences and PCR reaction conditions were as follows:

```
Tadh_HYG-F:
                                       (SEQ ID NO. 5)
5'-ATCTCCGGCCAGTCGTTTTTGCATGCGAACCCGAAAATGG-3'

POX4_HYG-R:
                                       (SEQ ID NO. 6)
5'-CTAAGGGTTTTTCCGGGGCTGCTAGCAGCTGGATTTCACT-3'
```

Step 1: 98° C. for 30 s
Step 2: 98° C. for 10 s, 55° C. for 10 s, 72° C. for 1 m 50 s, 5 cycles
Step 3: 98° C. for 10 s, 72° C. for 2 m, 25 cycles
Step 4: 72° C. for 5 m.

The obtained product was designated as HYG and confirmed by sequencing, as set forth in SEQ ID NO.7.

3. Amplification of upstream and downstream homologous recombination fragments. The template was the above genomic DNA, and the primer sequences were as follows:

```
POX4_Up-F:
                                       (SEQ ID NO. 8)
5'-CCCCCACCTTTTGTCTCTGG-3'

POX4_Up-R:
                                       (SEQ ID NO. 9)
5'-AACGGACACTAACTCCGTCG-3'

POX4_Down-F:
                                       (SEQ ID NO. 10)
5'-AGCCCCGGAAAAACCCTTAG-3'

POX4_Down-R:
                                       (SEQ ID NO. 11)
5'-GAGACGTGGGGGTAAGGTTG-3'
```

The PCR reaction conditions were as follows:
Step 1: 98° C. for 30 s
Step 2: 98° C. for 10 s, 55° C. for 10 s, 72° C. for 15 s, 5 cycles
Step 3: 72° C. for 5 m.

The obtained products were designated as POX4_Up and POX4_Down, respectively, and the PCR products were recovered after precipitation with ethanol, and the sequences thereof were set forth in SEQ ID NOs. 12 and 13.

4. PCR overlap extension to obtain a complete recombination template

The above four recovered and purified PCR fragments of SEQ ID NOs. 3, 7, 12 and 13 were overlap-extended to obtain a homologous recombination template, which was recovered and purified. The specific method was as follows:

the fragments ADH, HYG, POX4_Up and POX4_Down were added in equimolar amounts to serve as templates, the primers were POX4_Up-F and POX4_Down-R, and PrimeSTAR® HS high-fidelity DNA polymerase was used for PCR overlap extension. The PCR reaction conditions were as follows:

Step 1: 98° C. for 30 s
Step 2: 98° C. for 10 s, 55° C. for 10 s, 72° C. for 5 m, 5 cycles
Step 3: 72° C. for 8 m.

After gel electrophoresis, a recombinant fragment having a size of about 4.5 Kb was recovered and purified, and the sequence thereof was set forth in SEQ ID NO. 14.

FIG. 1 is a schematic diagram showing the replacement of gene POX4 with ADH and removal of the hygromycin resistance marker by homologous recombination.

Example 3

Transformation of Recombinant Transformant

1. Preparation of yeast electroporation competent cells

Yeast cells CCTCC M2011192 cultured overnight on a shaker at 30° C., 250 rpm were inoculated into 100 mL of the YPD medium of Example 1 until $OD_{620}$ reached 0.1. The cells were cultured under the same conditions until $OD_{620}$ reached 1.3, and then the cells were collected by centrifugation at 3000 g and 4° C. The cells were washed twice with ice-cold sterile water and collected, then re-suspended in 10 mL of 1M sorbitol solution which was pre-cooled on ice, and then collected by centrifugation at 4° C. and 1500 g and re-suspended in 1 mL of the above sorbitol solution. Aliquots of 100 μL of the cell suspension were for genetic transformation.

2. Electroporation of yeast competent cells

The above competent cells were added with 1 μg of the recovered and purified DNA fragment of SEQ ID NO. 14, and placed on ice for 5 min, then rapidly transferred to a 0.2 cm electroporation cuvette, and electroporated (BioRad, Micropulser™ Electroporator, transformation procedure SC2, 1.5 kV, 25 uFD, 200 ohms). The electroporated competent cells were quickly added with a mixture of 1 mL of YPD and 1M sorbitol (1:1, v/v), and cultured at 30° C., 200 rpm for 2 hours. The bacterial solution was collected, spread on a YPD medium plate containing 100 mg/L hygromycin B, and subjected to static culture at 30° C. for 2 to 3 days until single colonies grew.

Example 4

Screening of Recombinant Transformant

The single colonies obtained in Example 3 were picked and inoculated into a 2 mL centrifuge tube containing 1 mL of YPD medium (containing 100 mg/L hygromycin B), and cultured overnight at 250 rpm and 30° C. Colony PCR identification was performed the next day, and the primer sequences and PCR reaction conditions used were as follows:

Pox4_Up-F:
(SEQ ID NO. 15)
5'-GTGGTGGTAAGCCGACAGAA-3'

ADH-2R:
(SEQ ID NO. 16)
5'-AACAGCCTCAGCAGTGTCTC-3'

Step 1: 98° C. for 30 s
Step 2: 98° C. for 10 s, 55° C. for 10 s, 72° C. for 30 s, 5 cycles
Step 3: 72° C. for 5 m.

The positive strain screened by PCR was named 731HYG.

Example 5

Determination of the Ratio of Hydroxyl Acid to Dibasic Acid Produced by the Recombinant Strain with Resistance Marker 1. Screening method: single colonies of strain 731HYG were picked and inoculated into a 2 mL centrifuge tube containing 1 mL of the YPD medium (containing 100 mg/L hygromycin B) of Example 1, and cultured on a shaker at 30° C., 250 rpm for 1 day. The above bacterial solution was inoculated into a 500 mL shake flask containing 30 mL of the seed medium of Example 1 (containing 100 mg/L hygromycin B) with an inoculation amount of 3%, and cultured at 250 rpm, 30° C. until the $OD_{620}$ reached 0.8 (dilution by 30 folds). The seed solution was inoculated into a 500 mL shake flask containing 15 mL of the fermentation medium described in Example 1 with an inoculation amount of 20%, and the substrate in the fermentation medium was n-dodecane. The culturing was continued at 250 rpm, 30° C. until the end of the fermentation.

Further, the strain CCTCC M2011192 was used as control: the culture and fermentation methods were the same as above, except that the medium did not contain hygromycin B.

Samples of 0.5 g of the above fermentation broths were taken respectively, and subjected to GC detection by the method described in Example 1.4. The content of dodecanedioic acid and the mass ratio of the hydroxyl fatty acid impurity having 12 carbon atoms were calculated. The results were shown in Table 1 below.

2. Screening results: a candidate strain with an effectively decreased content of hydroxyl fatty acid impurity as compared with the original strain CCTCC M2011192 was obtained by screening, and was numbered as 731HYG.

TABLE 1

| Strain | CCTCC M2011192 | 731HYG |
|---|---|---|
| Yield of dodecanedioic acid (mg/g) | 147.3 | 148.2 |
| Mass ratio of the hydroxyl fatty acid impurity having 12 carbon atoms (%) | 1.32 | 0.75 |

The mass ratio of the hydroxyl fatty acid of the present invention was the mass percentage of the hydroxyl fatty acid to dodecanedioic acid. It can be seen from Table 1 that the mass ratio of the hydroxyl fatty acid impurity having 12 carbon atoms was decreased by 43.2%.

Example 6

Removal of the Resistance Marker

1. Preparation of a homologous recombination template for removing the resistance marker The DNA fragment for removing the resistance screening marker was amplified by PCR using PrimeSTAR® HS high-fidelity DNA polymerase with the genomic DNA of *Candida tropicalis* CCTCC M2011192 as a template. The primer sequences used were as follows:

Tadh-F:
(SEQ ID NO. 17)
5'-TAAACAAAACCTGGCGCCTC-3'

Tadh-R:
(SEQ ID NO. 18)
5'-AAAAACGACTGGCCGGAG-3'

The PCR reaction conditions were as follows:
Step 1: 98° C. for 30 s
Step 2: 98° C. for 10 s, 55° C. for 10 s, 72° C. for 30 s, 5 cycles
Step 3: 72° C. for 5 m.

The DNA fragment was recovered and purified by electrophoresis on 1% agarose gel, and the sequence was set forth in SEQ ID NO. 19.

The recovered and purified DNA fragments of SEQ ID NO. 19 and SEQ ID NO. 13 were added in equimolar amounts as templates, the primers were Tadh-F and POX4_Down-R, and PCR overlap extension was carried out using PrimeSTAR® HS high-fidelity DNA polymerase. The PCR reaction conditions were as follows:
Step 1: 98° C. for 30 s
Step 2: 98° C. for 10 s, 55° C. for 10 s, 72° C. for 45 s, 20 cycles
Step 3: 72° C. for 5 m.

After gel electrophoresis, a recombinant fragment having a size of about 600 bp was recovered and purified, and the sequence thereof was set forth in SEQ ID NO. 20.

2. Removal of the resistance marker

Freshly competent cells of strain 731HYG for electroporation were prepared, added with 0.3 µg of the recovered recombinant fragment of step 1, placed on ice for 5 min, and then rapidly transferred to a 0.2 cm electroporation cuvette pre-chilled on ice, and electroporated (supra, 1.5 kV, 25 uFD, 200 ohms). The electroporated competent cells were quickly added to a mixture of 1 mL of YPD and 1M sorbitol (1:1, v/v), and cultured at 30° C., 200 rpm for 2 hours. The bacterial solution was collected, spread on a plate with the YPD medium containing no antibiotics, and subjected to static culture at 30° C. for 2 to 3 days until single colonies grew.

3. Screening of a strain with the resistance marker removed

Single colonies were picked and inoculated separately on YPD plates with or without hygromycin (100 mg/L). The single colonies that could not grow on the medium containing antibiotics but could grow on the medium containing no antibiotics were picked and inoculated in a 2 mL centrifuge tube containing 1 mL of the YPD medium, and cultured overnight at 4° C. and 250 rpm. The next day, the strain was identified by colony PCR to determine whether the resistance screening marker was removed. The primers and PCR reaction conditions were as follows.

a) Primers: Tadh-F and POX4_Down-R;

The PCR reaction conditions were: 94° C. for 45 s; 94° C. for 25 s, 55° C. for 25 s, 72° C. for 2 m 15 s (30 cycles); 72° C. for 5 m; stored at 15° C.

b) Primers:

HYG-F:
(SEQ ID NO. 21)
5'-CTCGGAGGGCGAAGAATCTC-3'

HYG-R:
(SEQ ID NO. 22)
5'-CAATGACCGCTGTTATGCGG-3'

The PCR reaction conditions were: 94° C. for 45 s; 94° C. for 25 s, 52° C. for 25 s, 72° C. for 45 s (30 cycles); 72° C. for 5 m; stored at 15° C.

Only a fragment with 221 bp in length could be amplified using Tadh-F and POX4_Down-R, and the strain without the amplified fragments of HYG-F and HYG-R was the target strain from which the resistance marker was removed. In the target strain, the POX4 gene was replaced by ADH, and no resistance screening marker gene HYG was contained. Finally the strain was named 731.

Example 7

Determination of the Ratio of Hydroxyl Acid in the Production of Dibasic Acid by Recombinant Strain 731

Fermentation: The strains CCTCC M2011192 and 731 were inoculated separately into 2 mL centrifuge tubes containing 1 mL of the YPD medium described in Example 1, and cultured on a shaker at 30° C., 250 RPM for 1 day. The above bacterial solution was inoculated into a 500 mL shake flask containing 30 mL of the seed medium of Example 1 with an inoculation amount of 3%, and cultured on a shaker at 250 rpm, 30° C. for 36 to 48 h until the $OD_{620}$ reached 0.8 (dilution by 30 folds). The seed solution was inoculated into a shake flask containing 15 mL of the fermentation medium of Example 1 with an inoculation amount of 20%, and the substrate in the fermentation medium was n-dodecane. The shake cultivation was continued at 250 rpm, 30° C. until the end of the fermentation. Further, the strain CCTCC M2011192 was used as control, and the culture and fermentation methods were the same as above.

Samples of 0.5 g of the above fermentation broth were taken respectively, and subjected to GC detection by the method described in Example 1.4. The content of dodecanedioic acid and the mass ratio of hydroxyl fatty acid impurity were calculated. The results were shown in Table 2 below:

TABLE 2

| Strain | CCTC M2011192 | 731 |
| --- | --- | --- |
| Yield of dodecanedioic acid (mg/g) | 146.4 | 148.5 |
| Mass ratio of the hydroxyl fatty acid impurity having 12 carbon atoms (%) | 1.41 | 0.72 |

It can be seen from Table 2 that the mass ratio of the hydroxyl fatty acid impurity having 12 carbon atoms was decreased by 48.9% after removal of the resistance screening marker.

Extraction and Purification:

(1) The above fermentation broth was adjusted to have a pH of 8.4 with a sodium hydroxide solution with a mass concentration of 30%, added with water until the concentration of the long-chain dibasic acid was 8.5 wt %, heated to 45° C., and filtered with a ceramic membrane having a pore size of 0.05 μm [purchased from Suntar Membrane Technology (Xiamen) Co., Ltd.]. The ceramic membrane used had a membrane area of 0.84 m² and a pre-membrane pressure of 0.3 MPa. The membrane clear liquid was collected.

(2) The collected membrane clear liquid was decolorized by adding 5 wt % of powdered activated carbon (relative to the amount of the long-chain dibasic acid contained in the solution) at 60° C., and filtered to obtain a clear liquid.

(3) The clear liquid was further added with sulfuric acid to adjust the pH to 3.5, cooled to 30° C., and filtered to obtain a wet solid. The wet solid was washed with purified water 3 times the weight of the wet solid, filtered and then dried to obtain the primary product of dodecanedioic acid.

(4) The primary product of dodecanedioic acid was added with acetic acid at a concentration of 97% of 3.5 times the amount (relative to the weight of the primary product of dodecanedioic acid), heated to 85° C. for dissolution, added with 1% macroporous powdered activated carbon (relative to the weight of the primary product of dodecanedioic acid) for decolorization, kept at 85° C. for 1 hour, and hot filtered to obtain a clear liquid. The solution was cooled to 30° C. at a rate of 10° C./hour, and a dodecanedioic long-chain dibasic acid crystal solution was obtained, which was filtered to obtain a wet solid which was to be washed with water to remove the solvent, and dried to obtain the secondary product of dodecanedioic acid.

The purity of dodecanedioic acid and the content of the hydroxyl fatty acid impurity were determined and calculated using the method described in Example 1.4, as shown in Table 3 below:

TABLE 3

| Dodecane-dioic acid | Strain | CCTCCM2011192 | 731 |
|---|---|---|---|
| Primary product | Purity of dodecanedioic acid (%) | 97.58 | 98.34 |
|  | Content of hydroxyl fatty acid impurity having 12 carbon atoms (ppm) | 5860 | 3130 |
| Secondary product | Purity of dodecanedioic acid (%) | 98.82 | 99.77 |
|  | Content of hydroxyl fatty acid impurity having 12 carbon atoms (ppm) | 415 | 184 |

Example 8

Production of Decanedioic Acid by Fermentation of Strain 731

Fermentation: Strain 731 was inoculated into a 2 mL centrifuge tube containing 1 mL of the YPD medium of Example 1 and cultured on a shaker at 30° C., 250 RPM for 1 day. The above bacterial solution was inoculated into a 500 mL shake flask containing 30 mL of the seed medium of Example 1 with an inoculation amount of 3%, and cultured on a shaker at 250 rpm, 30° C. for 36 to 48 hours until the $OD_{620}$ reached 0.8 (dilution by 30 folds). The seed solution was inoculated into a shake flask containing 15 mL of the fermentation medium of Example 1 with an inoculation amount of 20%, and the substrate in the fermentation medium was n-decane. The shake cultivation was continued at 250 rpm, 30° C. until the end of the fermentation. Further, the strain CCTCC M2011192 was used as control, and the culture and fermentation methods were the same as above.

Samples of 0.5 g of the above fermentation broths were taken respectively, and subjected to GC detection by the method described in Example 1.4. The yield of decanedioic acid and the mass ratio of the hydroxyl fatty acid impurity having 10 carbon atoms were calculated. The results were shown in Table 4 below:

TABLE 4

| Strain | CCTCC M2011192 | 731 |
|---|---|---|
| Yield of decanedioic acid (mg/g) | 121.8 | 124.2 |
| Mass ratio of hydroxyl fatty acid impurity having 10 carbon atoms (%) | 0.92 | 0.56 |

It can be seen from Table 4 that the mass ratio of the hydroxyl fatty acid impurity having 10 carbon atoms was decreased by 39.1%.

The extraction and purification steps were the same as the extraction and purification steps of Example 7. The purities of the obtained primary and secondary products of decanedioic acid and the content of the hydroxyl fatty acid impurity having 10 carbon atoms were determined and calculated using the method described in Example 1.4, as shown in Table 5 below:

TABLE 5

| Decanedioic acid | Strain | CCTCC M2011192 | 731 |
|---|---|---|---|
| Primary product | Purity of decanedioic acid (%) | 99.04 | 99.57 |
|  | Content of hydroxyl fatty acid impurity having 10 carbon atoms (ppm) | 2380 | 1570 |
| Secondary product | Purity of decanedioic acid (%) | 99.41 | 99.88 |
|  | Content of hydroxyl fatty acid impurity having 10 carbon atoms (ppm) | 330 | 165 |

Example 9

Production of Hexadecanedioic Acid by Fermentation of Strain 731

Fermentation: Strain 731 was inoculated into a 2 mL centrifuge tube containing 1 mL of the YPD medium of Example 1 and cultured on a shaker at 30° C., 250 RPM for 1 day. The above bacterial solution was inoculated into a 500 mL shake flask containing 30 mL of the seed medium of Example 1 with an inoculation amount of 3%, and cultured on a shaker at 250 rpm, 30° C. for 36 to 48 hours until the $OD_{620}$ reached 0.8 (dilution by 30 folds). The seed solution was inoculated into a shake flask containing 15 mL of the fermentation medium of Example 1 with an inoculation amount of 20%, and the substrate in the fermentation medium was n-hexadecane. The shake cultivation was continued at 250 rpm, 30° C. until the end of the fermentation. Further, the strain CCTCC M2011192 was used as control, and the culture and fermentation methods were the same as above.

Samples of 0.5 g of the above fermentation broths were taken respectively, and subjected to GC detection by the method described in Example 1.4. The yield of hexadecanedioic acid and the mass ratio of the hydroxyl fatty acid impurity having 16 carbon atoms were calculated. The results were shown in Table 6 below:

TABLE 6

| Strain | CCTCC M2011192 | 731 |
|---|---|---|
| Yield of hexadecanedioic acid (mg/g) | 123.8 | 126.7 |
| Mass ratio of hydroxyl fatty acid impurity having 16 carbon atoms (%) | 3.08 | 1.96 |

It can be seen from Table 6 that the mass ratio of the hydroxyl fatty acid impurity having 16 carbon atoms was decreased by 36.4%.

The extraction and purification steps were the same as the extraction and purification steps of Example 7. The purity of the obtained primary and secondary products of hexadecanedioic acid and the content of the hydroxyl fatty acid impurity having 16 carbon atoms were determined and calculated using the method described in Example 1.4, as shown in Table 7 below:

TABLE 7

| Hexadecanedioic acid | Strain | CCTCC M2011192 | 731 |
|---|---|---|---|
| Primary product | Purity of hexadecanedioic acid (%) | 81.80 | 86.70 |
| | Content of hydroxyl fatty acid impurity having 16 carbon atoms (ppm) | 8975 | 7530 |
| Secondary product | Purity of hexadecanedioic acid (%) | 98.33 | 99.20 |
| | Content of hydroxyl fatty acid impurity having 16 carbon atoms (ppm) | 3009 | 1950 |

Example 10

The DNA fragment of SEQ ID NO: 14 as described in Example 2 was introduced into *Candida tropicalis* (CCTCC M203052) by homologous recombination, and the method to obtain a recombinant microorganism in which POX4 gene was replaced with ADH gene was the same as that in Example 3. The method of screening out single colonies was the same that in Example 4. The obtained positive strain was designated as 732HYG.

The fermentation method was the same as Example 5, and the strains CCTCC M203052 and 732HYG were used. After fermentation, samples of 0.5 g of the above fermentation broth were taken respectively, and subjected to GC detection by the method described in Example 1.4. The content of dodecanedioic acid and the mass ratio of hydroxyl fatty acid impurity having 12 carbon atoms were calculated as shown in Table 8. The results indicated, compared to the parent strain CCTCC M203052, the content of the hydroxyl fatty acid impurity in the dibasic acid produced by 732HYG was significantly reduced:

TABLE 8

| Strain | CCTCC M203052 | 732HYG |
|---|---|---|
| Yield of dodecanedioic acid (mg/g) | 134.6 | 133.5 |
| Mass ratio of the hydroxyl fatty acid impurity having 12 carbon atoms (%) | 1.24 | 0.58 |

Example 11

Recombination of ADH Gene at Optionally Selected Site in the Genome

The method of preparing templates for homologous recombination referred to Example 2. The following fragment was amplified using PrimeSTAR® HS high-fidelity DNA polymerase with the following primers:

```
Up-F:
                                        (SEQ ID NO: 23)
5'-TTAGACCGCCAGAGAAGGGA-3'

Up-R:
                                        (SEQ ID NO: 24)
5'-TGTCATTGCGTAACGTGGGA-3'

Down-F:
                                        (SEQ ID NO: 25)
5'-GTGGTGGGTTCCCAGCTTAT-3'

Down-R:
                                        (SEQ ID NO: 26)
5'-GGAGGTACCAACAATCCCCG-3'
```

The DNA fragment in Example 1 was used as template, and the PCR reaction conditions were as follows:

Step 1: 98° C. for 30 s
Step 2: 98° C. for 10 s, 55° C. for 10 s, 72° C. for 1 m 10 s, 30 cycles
Step 3: 72° C. for 5 m.

The resultant products were named as Up and Down respectively.

```
ADH-2F:
                                        (SEQ ID NO: 27)
5'-TCCCACGTTACGCAATGACAGTCTTGGTTGGTTTGCCAGC-3'

HYG-2R:
                                        (SEQ ID NO: 28)
5'-ATAAGCTGGGAACCCACCACGCTAGCAGCTGGATTTCACT-3'.
```

The template was SEQ ID NO: 14 which was diluted by a factor of $10^6$, and the PCR reaction conditions were as follows:

Step 1: 98° C. for 30 s
Step 2: 98° C. for 10 s, 55° C. for 10 s, 72° C. for 4 m, 5 cycles
Step 3: 98° C. for 10 s, 72° C. for 4 m, 25 cycles
Step 4: 72° C. for 5 m.

The obtained product was named as ADH-HYG.

The recovered and purified DNA fragments of Up, Down and ADH-HYG were added in equimolar amounts as templates, and the primers were SEQ ID NO: 23 and SEQ ID NO: 26. The PCR reaction conditions were as follows:

Step 1: 98° C. for 30 s
Step 2: 98° C. for 10 s, 55° C. for 10 s, 72° C. for 6 m 30 s, 20 cycles
Step 3: 72° C. for 5 m.

The obtained PCR product with a size of about 6 Kb was recovered and purified, and verified by sequencing, the sequence thereof was set forth in SEQ ID NO. 29.

1 μg of the above recovered and purified DNA fragment set forth in SEQ ID NO. 29 by PCR was transformed to CCTCC M 20111192, as described in Example 3. The recombinant screening referred to Example 4, and the primers and the PCR reaction conditions were as follows:

HR-F:
(SEQ ID NO: 30)
5'-TCATGATAGCCATCGGCCAC-3'

HR-R:
(SEQ ID NO: 31)
5'-CCACCAACCAGCCCCATTAT-3'

Step 1: 98° C. for 5 m
Step 2: 98° C. for 30 s, 55° C. for 30 s, 72° C. for 1 m 30 s, 30 cycles
Step 3: 72° C. for 5 m.

The positive strain selected by PCR, from which, compared to untransformed strains, a target fragment with a size of about 1.4 Kb could be amplified, was named as 733HYG.

The fermentation method was the same as Example 5, and the strains CCTCC M2011192 and 733HYG were used. After fermentation, samples of 0.5 g of the above fermentation broth were taken respectively, and subjected to GC detection by the method described in Example 1.4. The content of dodecanedioic acid and the mass ratio of hydroxyl fatty acid impurity having 12 carbon atoms were calculated as shown in Table 9. The results showed, compared to the parent strain CCTCC M2011192, the content of the hydroxyl fatty acid impurity in the dibasic acid produced by 733HYG was reduced by 38.9%, indicating that the content of hydroxyl acid impurity having 12 carbon atoms in the dibasic acid was significantly reduced relative to that in the dibasic acid produced by the parent strain without overexpressing ADH gene.

TABLE 9

| Strain | CCTCC M2011192 | 733HYG |
| --- | --- | --- |
| Yield of dodecanedioic acid (mg/g) | 144.9 | 145.6 |
| Mass ratio of the hydroxyl fatty acid impurity having 12 carbon atoms (%) | 1.26 | 0.77 |

From the above examples (Examples 7-11) for producing long-chain dibasic acids by fermentation with different fermentation substrates, it can be seen that the content of hydroxyl fatty acid impurity in the fermentation broth after fermentation was significantly decreased, and the content of hydroxyl fatty acid impurity can be decreased by at least 30% as compared with the parent strain, and overexpression of ADH gene together with attenuating POX4 gene (e.g. replacing POX4 gene with ADH gene) would further reduce the content of hydroxyl fatty acid impurity. Furthermore, further extraction and purification of the obtained dodecanedioic acid, decanedioic acid, and hexadecanedioic acid can further decrease the content of hydroxyl fatty acid impurity, and greatly reduces the difficulty of subsequent extraction and purification processes. Moreover, as an important raw material for nylon filaments, synthetic perfumes, engineering plastics, cold-resistant plasticizers, high-grade lubricating oils and polyamide hot melt adhesives and others, a dibasic acid product will be more conducive to the production and manufacture of downstream products and improve the quality of the downstream products as the content of hydroxyl fatty acid impurity decreases.

The invention claimed is:

1. A product, which is a recombinant long-chain dibasic acid producing microorganism, having increased alcohol dehydrogenase activity and decreased acyl-CoA oxidase activity, wherein, in the recombinant microorganism, PDX4 gene is replaced with one or more copies of ADH gene, wherein the recombinant long-chain dibasic acid producing microorganism produces a long-chain dibasic acid with a low content of hydroxyl acid impurity.

2. The product of claim 1, wherein the recombinant long-chain dibasic acid producing microorganism:
   (i) is selected from the group consisting of *Corynebacterium, Geotrichum candidum, Candida, Pichia, Rhodotroula, Saccharomyces* and *Yarrowia;*
   (ii) is yeast; or
   (iii) is *Candida tropicalis* or *Candida sake.*

3. The product of claim 1, wherein in the recombinant microorganism one copy of PDX4 gene in the genome is replaced with one copy of ADH gene.

4. The product of claim 2, wherein the nucleotide sequence of the ADH gene is set forth in SEQ ID NO: 3.

5. The product of claim 1, wherein the long-chain dibasic acid is:
   (i) selected from the group consisting of C9 to C22 long-chain dibasic acids;
   (ii) selected from the group consisting of C9 to C18 long-chain dibasic acids;
   (iii) one or more selected from the group consisting of C10 dibasic acid, C11 dibasic acid, C12 dibasic acid, C13 dibasic acid, C14 dibasic acid, C15 dibasic acid and C16 dibasic acid;
   (iv) at least one or more of C10 to C16 dibasic acids, or at least one or more of n-C10 to C16 dibasic acids; or
   (v) at least one or more selected from the group consisting of sebacic acid, undecanedioic acid, dodecanedioic acid, tridecanedioic acid, tetradecanedioic acid, pentadecanedioic acid and hexadecanedioic acid.

6. The product of claim 1, wherein the content of hydroxyl acid impurity in the long-chain dibasic acid is more than 0 and less than 10,000 ppm, 4,000 ppm, 300 ppm or less, wherein the hydroxyl acid impurity comprises a hydroxyl fatty acid having one carboxyl group.

7. The product of claim 1, wherein recombinant long-chain dibasic acid producing microorganism produces a fermentation broth in a process for producing a long-chain dibasic acid by fermentation, wherein the fermentation broth contains hydroxyl acid impurity, wherein the content of the hydroxyl acid impurity is less than 3%, 2%, 1.5%, 1.3%, 1.2%, 1.1%, 1.0%, 0.9%, 0.8%, 0.7%, 0.6%, 0.5%, 0.4%, 0.3% or less, wherein the percentage is the mass percentage of the hydroxyl acid impurity to the long-chain dibasic acid in the fermentation broth.

\* \* \* \* \*